(12) United States Patent
Simon

(10) Patent No.: US 6,928,318 B2
(45) Date of Patent: Aug. 9, 2005

(54) SYSTEM AND METHOD FOR ASSESSING THE PERFORMANCE OF A PHARMACEUTICAL AGENT DELIVERY SYSTEM

(75) Inventor: Adam J. Simon, Langhorne, PA (US)

(73) Assignee: Merck & Co., Inc., Rahway, NJ (US)

( * ) Notice: Subject to any disclaimer, the term of this patent is extended or adjusted under 35 U.S.C. 154(b) by 522 days.

(21) Appl. No.: 09/862,850

(22) Filed: May 22, 2001

(65) Prior Publication Data

US 2002/0010415 A1 Jan. 24, 2002

Related U.S. Application Data

(60) Provisional application No. 60/206,121, filed on May 22, 2000.

(51) Int. Cl.[7] ............................................... A61N 1/30
(52) U.S. Cl. ....................................................... 604/20
(58) Field of Search .......................... 604/19, 20, 890.1, 604/21, 501, 113, 291; 607/3, 901

(56) References Cited

U.S. PATENT DOCUMENTS

| | | | | | |
|---|---|---|---|---|---|
| 4,383,529 A | * | 5/1983 | Webster | ........................ | 604/20 |
| 4,406,658 A | * | 9/1983 | Lattin et al. | ................... | 604/20 |
| 4,702,732 A | * | 10/1987 | Powers et al. | ................. | 604/20 |
| 5,273,525 A | | 12/1993 | Hofmann | | |

(Continued)

FOREIGN PATENT DOCUMENTS

| | | |
|---|---|---|
| WO | WO98/43702 | 10/1998 |
| WO | WO99/01157 | 1/1999 |
| WO | WO99/01158 | 1/1999 |
| WO | WO99/01175 | 1/1999 |

OTHER PUBLICATIONS

Jaroszeski et al., *Advanced Drug Delivery Reviews*, 35, 1999, pp. 131–137.
Widera et al., *J. Immunology*, 2000, pp. 4635–4640.
Vicat et al., *Human Gene Therapy*, 2000, pp. 909–916.
Aihara and Miyazaki, *Nature Biotechnology*, 1998, pp. 867–870.
Ros, et al., *Nature Biotechnology*, 1998, pp. 168–171.
Muramatsu, et al., *Biochem. Biophys. Res. Comm.*, 1997, pp. 45–59.
Zhang, et al., *Biochem. Biophys. Res. Comm.*, 1996, pp. 633–636.
Nishi, et al., *Cancer Res.*, 1996, pp. 1050–1055.
Heller, et al., *FEBS Letters*, 1996, pp. 225,228.
Titomirov, et al., *Biochem. Biophys. Acta*, 1991, pp. 131–134.
Mathiesen, *Gene Therapy*, 1999, pp. 508–514.

(Continued)

*Primary Examiner*—Manuel Mendez
(74) *Attorney, Agent, or Firm*—Duane Morris LLP

(57) ABSTRACT

A system and method for assessing the performance of a system for delivering a pharmaceutical agent to a portion of a body. A pair of electrodes are applied to the portion of the body. A pharmaceutical agent is infused into the portion of the body and the electrodes are energized by a signal generator, electrically stimulating the portion of the body. The voltage and current delivered to the portion of the body are measured using a data acquisition system thereby generating electrical parameter data. An immune response, gene expression level or other biological response to the pharmaceutical agent is measured and the electrical test data is correlated with the biological response to assess the performance of the system.

24 Claims, 16 Drawing Sheets

U.S. PATENT DOCUMENTS

| | | |
|---|---|---|
| 5,439,440 A | 8/1995 | Hofmann |
| 5,501,662 A | 3/1996 | Hofmann |
| 5,507,724 A | 4/1996 | Hofmann et al. |
| 5,515,848 A | 5/1996 | Corbett, III et al. |
| 5,545,130 A | 8/1996 | Hofmann et al. |
| 5,676,646 A | 10/1997 | Hofmann et al. |
| 5,702,359 A | 12/1997 | Hofmann et al. |
| 5,704,908 A | 1/1998 | Hofmann et al. |
| 5,810,762 A | 9/1998 | Hofmann |
| 5,869,326 A | 2/1999 | Hofmann |
| 5,968,006 A | 10/1999 | Hofmann |
| 5,983,131 A | 11/1999 | Weaver et al. |
| 6,047,208 A * | 4/2000 | Flower ................. 604/20 |
| 6,654,636 B1 * | 11/2003 | Dev et al. ............... 604/21 |

OTHER PUBLICATIONS

Bureau, et al., *Importance of Association Between Permeablization and Electrophoretic Force: for Intramuscular DNA Electrotransfer*, Biochimica et Biophysica Acta, vol. 1474, No. 3, pp 353–359 (May 1, 2000).

Oshima, et al., *Targeted Gene Transfer to Corneal Endothelium in vivo by Electric Pulse*, Gene Therapy, vol. 5, No. 10, pp 1347–1354 (Oct., 1998).

Zhang, et al., *In Vivo Transdermal Delivery of Large Molecules by Pressure–Mediated Electroincorporation and Electroporation: A Novel Method for Drug and Gene Delivery*, Bioelectrochemistry and Bioenergetics, vol. 42, pp 283–292 (1997).

* cited by examiner

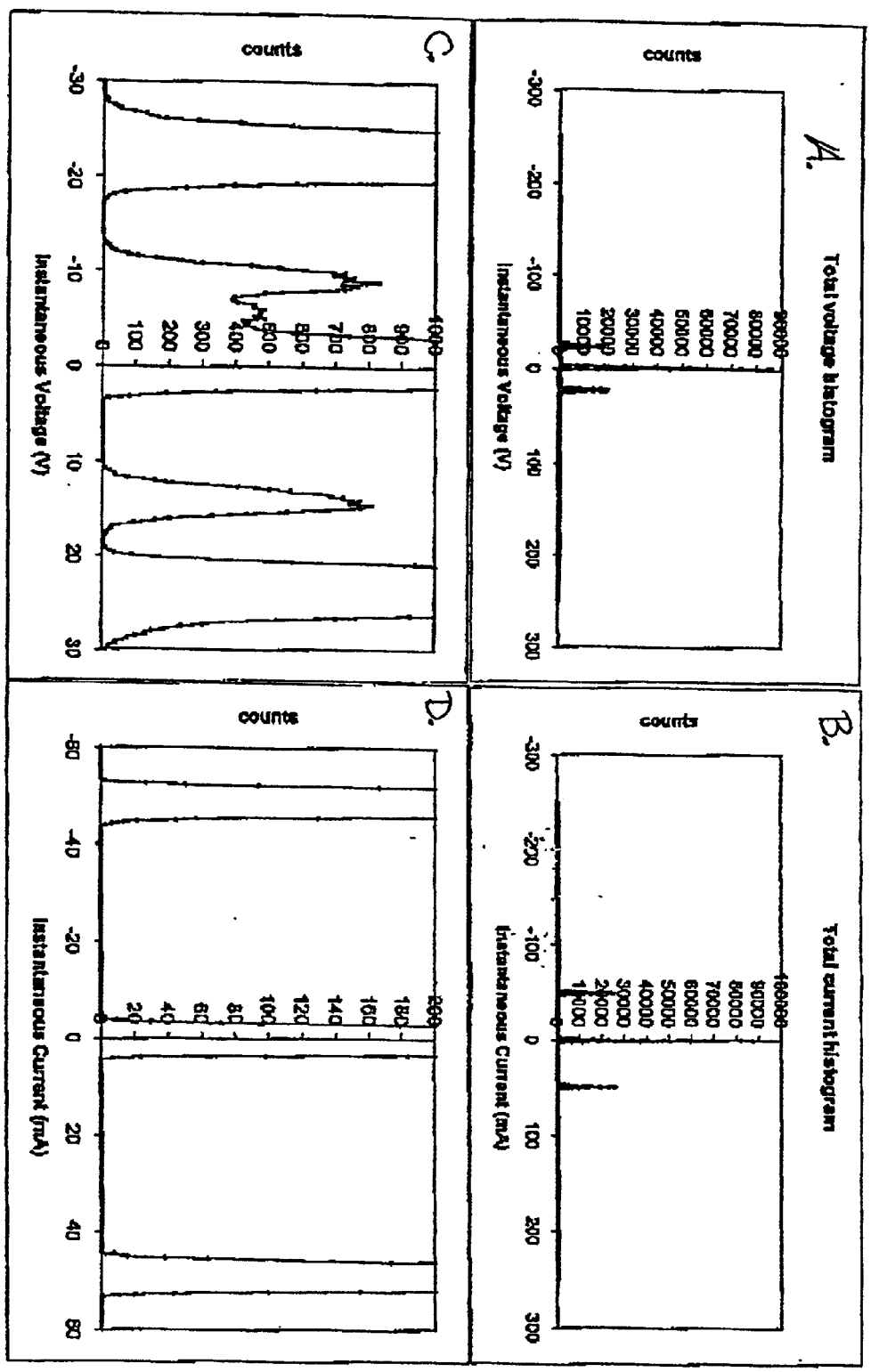
FIGURE 11A-D

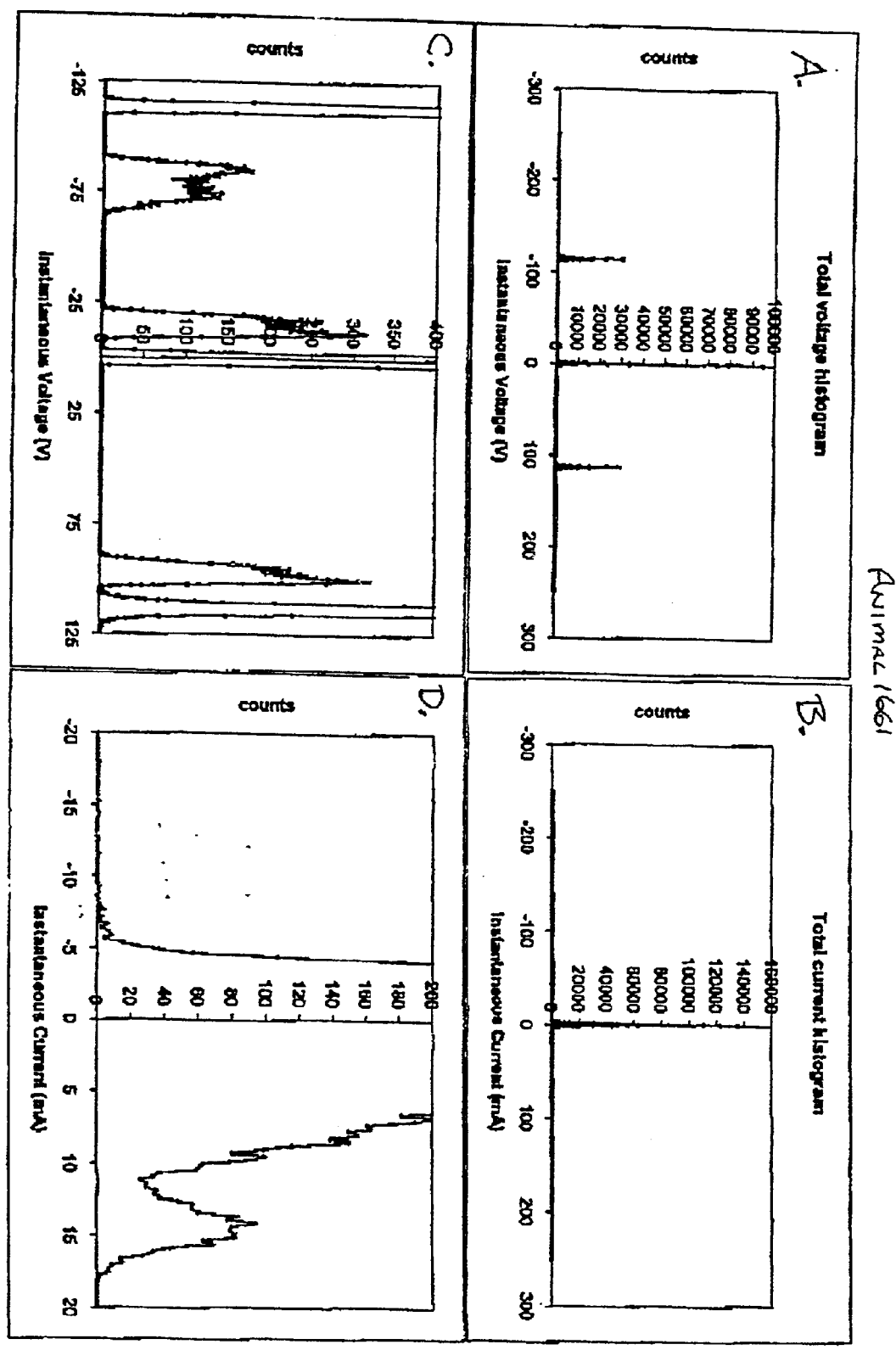
FIGURE 13A-D

SYSTEM AND METHOD FOR ASSESSING THE PERFORMANCE OF A PHARMACEUTICAL AGENT DELIVERY SYSTEM

This application claims priority of U.S. Provisional Application Ser. No. 60/206,121, filed May 22, 2000.

BACKGROUND OF THE INVENTION

1. Field of the Invention

The invention relates to the delivery of electromagnetic energy to living tissues, particularly in conjunction with the infusion of pharmaceutical agents. Apparatus and methods are provided for applying electromagnetic energy, by establishing field strength and current conditions including certain variations in the electrical parameters, and for measuring field and current parameters locally. The invention also relates to electrical stimulation ("electrostimulation") of host tissue to enhance in vivo cellular delivery of pharmaceuticals, such as nucleic acids and other pharmaceutical entities, including but not limited to proteins and small organic or inorganic molecules, and for assessing the effects.

An aspect of the invention relates to electrostimulation of host tissues, especially skeletal muscle, which relies on application of an electric stimulus utilizing partially insulating electrodes and similar arrangements that limit current amplitude in the tissue. The current in the electrostimulation site preferably is limited to less than the tissue would conduct, due to its electrical resistance, if placed in direct conductive contact with electrodes at a particular potential difference. This can be accomplished in alternative ways according to the disclosure.

The invention provides enhanced delivery and/or expression of a transgene of interest while also minimizing certain undesirable effects such as involuntary muscle movements associated with the use of conducting electrodes.

2. Description of the Related Art

Studies have shown that applied electrical energy can affect a biological membrane, in that a sufficient application of energy increases the permeability of the membrane and thus allows solutions to diffuse through a membrane or tissue more readily to achieve a desired effect. Generally, this phenomena is associated with iontophoresis, electrophoresis or electroporation (collectively "electrical stimulation" or "electrostimulation").

Iontophoresis generally concerns the introduction of an ionized substances through an intact membrane such as the skin, by application of a direct electric current. The current presumably entrains the ions and/or increases ion mobility in the tissue. Electrophoresis concerns the migration of ions in a fluid or gel under influence of an electric field. In electroporation, an electric field (often pulsed) and the associated induced current, induce microscopic pores to form in a membrane, typically a cell membrane. These pores are commonly called "electropores" and the process of forming them is electroporation. A potential application of electroporation is that solutions such as pharmaceutical agents, molecules, ions, and/or water can pass more readily from one side of the membrane to the other through the electrically generated pores. The pores preferably persist temporarily during application of the field. After application of the field, the pores should close or heal within a short period of time. However, the healing time is dependant on the amplitude and duration of the electrical stimulation, and it is possible to damage tissue permanently by application of too high an instantaneous power level and/or too long a duration of stimulation. The damage could be due to formation of untenably large or numerous pores, or resistive heating of the tissue, or both.

Electrically induced pores are readily observed in vitro. Cells in a solution are substantially independent of one another and are exposed to view. However, it may be difficult to observe temporary electropores in an in vivo setting, assuming that they occur. More and less-conductive tissues surround any given cell and often have an orientation peculiar to the tissue type. Thus discontinuities in conductivity presumably affect the manner in which electromagnetic energy is coupled to tissues, locally affecting the voltage gradient and current density. Tissues surrounding an observation site in vivo also would interfere with visual observation. Perhaps for these reasons, no exemplary in vivo study of electroporation is currently known to the inventor.

Without a relatively detailed understanding of the pertinent operative parameters, it may be difficult to assess and potentially to apply electrical stimulation ("electrostimulation") of tissues to useful ends. Assuming that current and voltage are the primary operational parameters of interest, there are still innumerable ways in which current and voltage might be applied. A particular voltage or current might prove desirable or a particular power level might be needed. The voltage, current and/or power may have minimum and maximum values or a particular relationship. A time varying component might be critical, and various waveforms might be tried, at a frequency from DC (direct current) into radio frequencies. A time varying electrical stimulation might also prove beneficial for one purpose or another, for example varying a pulse rate, duty cycle, AC frequency or the like. The frequency, pulse rate, duty cycle or the like might be linearly varied, periodic or exponential. Periodic wave forms may or may not have a DC bias, and can be shaped as sine waves, sawtooth or triangle waves, square waves, square pulses of any desired duty cycle, exponentially-decaying or charging pulses, etc. Any of these waveform types might be applied continuously or in bursts or pulse trains. It would be advantageous to determine the effects of these different possibilities and to identify particular combinations that have a potentially useful application.

In electrical stimulation of tissues, contact and non-contact apparatus are possible. In a contact apparatus, a signal is applied by physically contacting a target tissue site using conductive electrodes attached on opposite sides of the target site. In a non-contact apparatus, an electric or magnetic field can be generated using electrodes or coils that are likewise disposed on opposite sides of the site. In the contact example, the tissue may have a reactive component (capacitance or inductance) and the conductivity of the tissue may change over time due to the effects of the application of energy (e.g., due to heating), but in general the electrical response of the tissue is according to Ohm's law. The current conducted through the tissue is proportional to the voltage, the specific proportion being the resistance of the tissue. There are inherent limitations in this fact. Assuming conductive contact, one normally cannot independently control the applied voltage without a corresponding effect on current, and vice versa. Increasing voltage and/or current in tissues lead to increased joule heating and potential spasmodic muscular contraction. In a non-contact example (limited to an externally applied electric field), little current is conducted, although there may be an increase in ion mobility and oscillation, depending on frequency.

Although electroporation, iontophoresis, electrophoresis and the like have been identified, there is little real understanding of the parameters involved. Attempts to make use of the phenomena have had mixed results. There has been little indication of a clear direction for development. It would be advantageous to improve understanding of these phenomena and to make progress in the development of protocols for administering pharmaceutical agents to tissues under electromagnetic influence. It would be most advantageous if the electrical and biological aspects were understood to the extent that protocols could be suggested for treatments involving specific pharmaceutical agents. To date, attempts to optimize electrical stimulation to achieve a desired result have been limited to empirical adjustments, for example of pulse parameters. Empirical adjustments can be an unsure proposition. Such empirical adjustments may logically assume that electrical energy at higher power levels achieves more extensive pore formation and thus better results than at lower levels. However, this is not a direct relationship and in any event there are drawbacks to increasing output power, such as potential gene integration, tissue damage and discomfort for the patient or host.

An improved method is needed for controlling, measuring and assessing the performance of pharmaceutical agent delivery systems utilizing in vivo electrical stimulation, that can address the needs to apply an optimal signal while preserving the host's comfort and avoiding integration and tissue damage. Such a system needs the capability to vary the application of energy in a manner that is variable over a useful range of voltage, current, waveshape, duty cycle, cadence or repetition and other factors. The system also should accurately measure the voltage and current levels under load from the tissues so as to monitor and potentially to control the application of electrical stimulation at the appropriate micro or macro level. The system should advantageously produce sampling information or otherwise communicate meaningfully with processes that permit correlation of the electrical parameters to the effectiveness of the treatment. The effectiveness of the treatment in that context should be assessed beyond the time of treatment, by means other than monitoring electrical parameters per se. Preferably, the system should be optimized for planning and testing electrical parameters, including the testing of options which are sensitive to considerations that are ancillary to the formation of pores in membranes. Such ancillary considerations may include, for example, the potential for gene integration, tissue damage or the comfort of the host (subject). The system and its testing facilities and methods should be optimized for adapting the technique to treatment using particular therapeutic agents, namely by facilitating the planning and testing of iontophoresis and electrophoresis regimes in connection with a variety of therapeutic agents.

WO 98/43702 (see also Mathiesen, 1999, *Gene Therapy* 6: 508–514) disclose in vivo electrostimulation of skeletal muscle within a calculated electric field strength ranging from about 25 V/cm to about 250 V/cm. The electric field strength was calculated simply as a two dimensional voltage gradient, namely the potential difference (V) between the conductive electrodes, divided by the distance (cm) between the electrodes. The discussion does not delve into the electrical current resulting at a given voltage, from conductive coupling of electrodes to the tissue, or how or why the voltage gradient and the current density might advantageously be distributed, or how these factors might affect charge migration or other considerations that could conceivably have an effect on the technique.

WO 99/01158, WO 99/01157 and WO 99/01175 disclose the use of low voltage for a long duration to promote in vivo electrostimulation of naked DNA. An electric field strength or voltage gradient of about 1 V/cm to about 600 V/cm is disclosed, depending upon the target tissue. This encompasses a relatively expansive range from minimal effect to potentially injurious levels. However, even higher voltage gradients have been proposed.

U.S. Pat. No. 5,810,762, U.S. Pat. No. 5,704,908, U.S. Pat. No. 5,702,359, U.S. Pat. No. 5,676,646, U.S. Pat. No. 5,545,130, U.S. Pat. No. 5,507,724, U.S. Pat. No. 5,501,662, U.S. Pat. No. 5,439,440 and U.S. Pat. No. 5,273,525 disclose electroporation/electrostimulation methodology and related apparatus wherein it is suggested that a useful electrical field strength range within the respective tissue is from about 200 V/cm to about 20 KV/cm. U.S. Pat. Nos. 5,968,006 and 5,869,326 further suggest that electric field strengths as low as 100 V/cm are useful for certain in vivo electrostimulation procedures.

Jaroszeski et al. (1999, *Advanced Drug Delivery Reviews* 35: 131–137) review the present landscape of in vivo electrically mediated gene delivery techniques. The authors emphasize previous success with delivery of chemotherapeutic agents to tumor cells and discuss some of the early results in this field.

Titomirov et al. (1991, *Biochem Biophys Acta* 1088: 131–134) delivered two plasmid DNA constructs subcutaneously followed by electrical stimulation of skin folds, generating an electric field strength from 400 V/cm to 600 V/cm.

Heller et al. (1996, *FEBS Letters* 389: 225–228) delivered plasmid DNA expressing two reporter genes to rat liver tissue by generation of high voltage pulses (11.5 KV/cm) rotated through a circular array of electrodes.

Nishi et al. (1996, *Cancer Res.* 56: 1050–1055) delivered plasmid DNA expressing a reporter gene to rat brain tissue. The authors utilized an electric field strength of approximately 600 V/cm.

Zhang et al. (1996, *Biochem. Biophys. Res. Comm.* 220: 633–636) delivered plasmid DNA transdermally to mouse skin with 120V pulses to the skin folds wherein the distance between the electrodes was only about 1 mm.

Muramatsu et al. (1997, *Biochem. Biophys. Res. Comm.* 223: 45–49) reported transfection of mouse testis cells with plasmid DNA via 100 V pulses with a 10 mS pulse duration.

Rols et al. (1998, *Nature Biotechnology* 16(2): 168–171) reported transfection of mouse tumor cells with plasmid DNA by applying voltages from about 300 to 400 V across a 4.2 mm spacing of the electrodes.

Aihara and Miyazaki (1998, *Nature Biotechnology* 16: 867–870) reported in vivo expression of (β-gal in mouse muscle tissue by delivering a square waveform pulse (50 mS duration) at constant voltage (60V) with the distance between the electrodes being 3–5 mm.

Vicat et al. (2000, *Human Gene Therapy* 11: 909–916) show that high voltage (900 V), short pulse (100 µS) electrostimulation protocols result in prolonged expression within targeted cells, in this case mouse muscle cells.

Widera et al (2000, *J. Immunology* 164: 4635–4640) apply 100 volts over a 5 mm distance with conducting electrodes to deliver hepatitis B surface antigen, HIV gag and env encoding DNA vaccines in vivo to mouse and guinea pigs.

Generally, the teachings of the prior art lack a rigorous investigation of the formation of electropores in tissue from the aspect of an electrical circuit, wherein the tissue is treated as a load to which a signal is applied. The application of electrical power to the tissue can be characterized not only by a coupling of electrical power to the tissue at a given voltage gradient, but also has other aspects. These include but are not limited to the current coupled to the tissue, which together with voltage determines power dissipation, how the coupling is effected spatially, which determines current distribution and in particular local current density, and various issues of timing. Furthermore, the prior art fails to adequately address ancillary aspects of the treatment, such as the muscle contractions that can be induced with the application of current to tissue. Such aspects can render a treatment tolerable or intolerable from a clinical perspective.

The foregoing prior art shows that relatively vigorous voltages and correspondingly substantial currents (based on the electrical resistance of the tissue) have at times been studied for potential effects on gene expression. Possible tissue damage concerns may favor using arrangements with modest electrical power dissipation in the tissue. However, despite work in the field of low voltage-based electrostimulation of skeletal muscle with conducting electrodes, there remains a need to eliminate the unpalatable features associated with the process, including severe involuntary muscle movements, while obtaining any biological advantages of the process. There also remains a need to distinguish and refine the operative parameters of the treatment, including by analysis of the process as an electrical circuit with the tissue coupled electrically to the signal source in particular ways and with a volume of tissue, and/or parallel conductive paths in the tissue, being treated as the electrical load. The present invention provides apparatus and methodology to address and meet these needs.

SUMMARY OF THE INVENTION

The invention provides a method and apparatus in which it is possible to set up and run electrical stimulation processes including delivery of one or more pharmaceutical agents in vivo, to record the electrical treatment conditions and results achieved, and to assess the performance of the processes in a manner that directly reflects and therefore permits assessment of the effectiveness of the processes in delivering pharmaceutical agents to living tissues. The invention is particularly applicable to electrical stimulation of tissue to improve the extent to which a genetic pharmaceutical comprising a plasmid can be taken up and produce a derived gene product for inducing an immune response or other biological response in the patient or host.

A pair of electrodes coupled to a stimulation and measurement unit are applied to a portion of a body, namely an animal (for example a mammal or a human) or a plant. A pharmaceutical agent is infused into the portion of the body, typically but not necessarily by injection at the area of the electrodes. The electrodes are energized by a signal generator, electrically stimulating the portion of the body using a predetermined driving signal. The driving signal can have preset parameters relating to one or more of voltage, current, and timing, such as pulse width, shape, duty cycle or repeat cadence. The signal generator and/or a driving amplifier coupled to the signal generator are controlled using feedback controls that can be based on voltage, current, power and timing considerations. The voltage and current delivered to the portion of the body are measured using a data acquisition system to collect time samples, thereby generating electrical parameter data which is recorded and stored. Gene expression levels, immune response or other desired biological responses to the pharmaceutical agent are measured, preferably at several points in time subsequent to the electrical stimulation. Advantageously, this process involves infusing the portion of the body with a marker comparable to the pharmaceutical being tested, and periodically assessing the concentration of the marker or its products in the host's system. The pharmaceutical agent can be introduced or suffused through the tissues subjected to treatment (generally "infused") in local or generally systemic ways. The electrical test data represented by the sampling is cross correlated with the gene expression data and/or immune system response to assess the performance of the system. In this way an optimal regime can be determined and executed for pharmaceutical agents having different and potentially unique attributes.

According to an inventive aspect, electrical stimulation is effected by application of a particular electrode apparatus to deliver the electrical stimulation treatment to the host. This technique involves limiting the current levels applied to the host while maintaining the current level to at least a predetermined minimum. Preferably, the current permitted to flow is maintained at least at the predetermined minimum while applying a voltage gradient that is substantially in excess of the voltage that would produce the predetermined minimum current under Ohm's law. This can be accomplished in a contact electrode arrangement according to an inventive aspect of the invention, by applying a dielectric to metallic electrodes such that the dielectric separates the electrodes from direct contact with the tissue. Alternatively, an insulating coating can be provided on the electrodes, in such a way that the insulating coating is not fully effective to electrically insulate the electrodes from the tissue. In one embodiment, a substantially insulating (non-conductive) material is applied to an electrode for piercing the tissue, having a sharp point or edge. The insulating material tends to become very thin or to fail at limited areas in the immediate area of the point or edge, thereby limiting contact between the metallic electrode and the tissue, and limiting current, by incompletely insulating the tissue from the current.

In a preferred arrangement, dielectric coated electrodes are employed, each of the electrodes of a pair having a conductive body portion, for example of metal, and a partially conductive coating applied to a surface of the conductive body portion. The partially conductive coating over the area of the electrode in contact with the tissue preferably has an impedance in the range of 1 K$\Omega$ to 10 M$\Omega$, in series with the tissue or load. This series impedance is subject to variations along local circuit paths. Advantageous coatings comprise Teflon fluorocarbons, especially PFA or possibly PTFE, xylenes and/or other poor electrical conductors such as insulating polymers. The conductivity of such materials can be adjusted by mixing with a greater or lesser proportion of fine carbon black, graphite, fine metal powder or the like to control conductivity and/or to limit conductive contact with tissues to an array of distributed sites that are individually small compared to the electrode dimensions. In the alternative, the partially conductive coating can be partially formed of enamel paint and optionally one or more clear coats.

The invention also relates to an electrical stimulation apparatus for delivering an electrical stimulation treatment to a portion of a body of a patient or host. The apparatus comprises a signal generator having an output to which a pair of electrodes are coupled as described above. Each electrode comprises a conductive body portion, and a partially conductive coating applied to a surface of the conductive body portion. The coating resides in the circuit between the output of the signal generator and the tissue, and limits the applied current. In this context, "partially conductive" and "partially insulating" are used substantially synonymously. The terms refer to the extent of coupling between metallic electrodes maintained at a particular voltage and an adjacent tissue site between the electrodes. Thus an electric field is applied across the tissue while restricting current to a level that preferably achieves an electrical stimulation effect without substantial discomfort, muscle spasms or undue joule heating.

The signal generator preferably comprises an arbitrary waveform signal generator for generation of signals of selected shape in time and a signal amplifier. The amplifier output is preferably configurable in one of a constant current and constant voltage feedback control mode, and in a preferred embodiment is controllable for constant average current, or constant average voltage in either a moderate or high voltage range. The output also can be controlled to maintain a particular power output (voltage times current or watts). The signal can be applied directly from the output of a controlled driver amplifier or the feedback sensing signal (s) can be taken or derived from the tissue of from another point in the circuit. In the case of a time varying signal, the circuit preferably filters the feedback sense signal to maintain a predetermined average level of current, voltage, power or other parameter. The control is preferably electrical but can also be based partly on other parameters such as tissue temperature.

The apparatus preferably comprises or has a mounting for guiding an injecting needle or cannula, which can be positioned to discharge a pharmaceutical agent precisely into a space between the two electrodes. Preferably, a needle/electrode holder is provided with a plurality of angular guide holes for guiding the needle and electrodes into the proper orientation with respect to the portion of the body and with respect to the electrodes. The electrodes can be arranged in an array.

Another inventive aspect concerns a method for delivering a pharmaceutical agent to a portion of a body of the host. The method involves contacting the portion of the body with at least one electrode having a dielectric material or an insulating layer that is not completely effective (e.g., due to adjustment of its conductivity or perhaps the inclusion of isolated gaps in the continuous coverage of the electrode) or a partially conductive outer surface. The portion of the body is infused with the pharmaceutical agent by any operative method of infusion, preferably by injection. The portion is then electrically stimulated using a signal generator coupled to the electrode and at least one other electrical contact site, which can be an opposed electrode provided in association with the electrode coupled to the insulating layer. The signal generator is operable to deliver an at least partially periodic signal to the electrode. The signal generator preferably operates in a constant voltage mode at about 150 volts peak to peak and delivers a charge in the range of 5–20 millicoulombs (preferably 5–8 mC) during each cycle. Effectively, the spaced electrodes and the tissue between them (normally muscle tissue having striations oriented parallel to a line between the electrodes) form a capacitor that is alternatively charged and discharged. The observed instantaneous peak current is about 15–20 mA; and the RMS average current is substantially less. It has been observed that some minimal RMS current needs to be maintained to achieve iontophoresis, electrophoresis and/or electroporation effects. For effectiveness it is desirable to employ a dielectric material or semi-conducting material for the electrode coating because a relatively good insulating coating, which cuts all current out, has been found to reduce or eliminate the beneficial effects obtained.

Another inventive aspect concerns an electrical stimulation apparatus for delivering an electrical stimulation treatment to a portion of a body having separate sources of electrical stimulation. A first signal generator is coupled to a pair of conductive electrodes. A second signal generator is coupled to a pair of partially conductive electrodes. An injecting needle or cannula, can be positioned to discharge a pharmaceutical into a space between the two pairs of electrodes. Preferably, a needle/electrode holder is provided with a plurality of angular guide holes for guiding the needle and electrodes into the proper orientation with respect to the portion of the body and with respect to the electrodes. The first signal generator is preferably an arbitrary waveform signal generator for generation of signals of selected shape in time and a signal amplifier (for example short pulses at a relatively low voltage for delivering instantaneous peak current of about 15–20 mA). The second signal generator is also preferably an arbitrary waveform signal generator for generation of signals of selected shape in time and a signal amplifier (for example low frequency sine wave signals at 100 volts for 10 seconds, yielding substantially no current flow). Both amplifier outputs are preferably configured in one of a constant current and constant voltage feedback control mode, respectively.

Coupling a signal to a "pair" of electrodes as discussed herein encompasses any configuration in which at least two or more opposed electrodes or discrete conductive paths are provided and are driven using the same or different driving signals. Thus, an array of separate or coupled anode and cathode electrodes can be provided and can be coupled to one another or driven from different specific signals. Individual electrodes in opposed pairs can be provided and interleaved or otherwise placed in an array. The electrodes can be subdivided to provide discrete or distributed levels of conductive contact with the tissue, so as to provide current paths that subtend the volume of tissue into which the agent has been infused.

The invention provides methods of electrical stimulation of host tissue, preferably skeletal muscle, to promote in vivo cellular delivery of nucleic acid molecules and other pharmaceutical entities. The nucleic acid molecules utilized in conjunction with the electrostimulation methodology and related apparatuses may be directly administered to a vertebrate host in vivo, including mammals such as primates and humans. The preferred host is in fact a mammal, such as a nonhuman primate, while an especially preferred host is a human.

A specific embodiment of the present invention relates to in vivo delivery of a nucleic acid transgene of interest to muscle cells using the electroporation apparatuses and methodology disclosed herein. Such a procedure is useful in DNA vaccination technology as well as gene therapy applications. The direct injection of plasmid DNA accompanied by electrostimulation of the muscle within the vicinity of the injection site is taught herein. More specifically, the electrostimulation methodology depends upon the apparatuses described herein, namely a partially conducting electrode set or plurality of sets of complementary electrodes used in conjunction with application of an exciting voltage coupled to the tissues by electrodes or the like that operated to limit the current coupled to the tissue. The electrode sets can be disposed in an array of more and less conductive electrodes or electrode areas (e.g., interspersed relatively more conductive and relatively more insulating surfaces of the electrodes). This arrangement provides reduced overall current through the sample, as compared to the current density that would be provided by fully conductive electrode surfaces under Ohm's Law if the same voltage was coupled directly and conductively to the tissue. Reducing the current and associated charge density in the tissue (by use of partially conducting electrodes) permits enhanced delivery and/or expression of the transgene of interest while minimizing the otherwise expected deleterious side effects of applied electromagnetic energy, such as involuntary muscle movements, joule heating and similar results of methods associated with the use of conducting electrodes.

BRIEF DESCRIPTION OF THE DRAWINGS

There are shown in the drawings certain exemplary embodiments of the invention as presently preferred. It should be understood that the invention is not limited to the embodiments disclosed as examples, and is capable of variation within the scope of the appended claims. In the drawings.

FIG. 8 is a block diagram functionally illustrating the system of the invention and subdivided into action or stimulus and reaction or measurement sections.

FIGS. 11A, 11B, 11C and 11D show instantaneous voltage and current histogram analysis of the raw binary data file recorded during the treatment procedure for animal 1750. FIGS. 11A and 11B provide macroscopic views, while FIGS. 11C and 11D magnify the central portion of each histogram to reveal details invisible when viewing the overall histogram. The total absolute current was approximately $I_{tot}$=20 mA over a 10 second treatment or 200 mC charge.

FIGS. 13A, 13B, 13C and 13D show instantaneous voltage and current histogram analysis of the raw binary data file recorded during the treatment procedure for animal 1661. FIGS. 13A and 13B provide macroscopic views, while FIGS. 13C and 13D magnify the central portion of each histogram to reveal details invisible when viewing the overall histogram. The total absolute current (charge) delivered was approximately $I_{tot}$=0.8 mA ($Q_{tot}$≅8 mC) over the 10 second treatment.

DETAILED DESCRIPTION OF THE PREFERRED EMBODIMENTS

Figure 1:
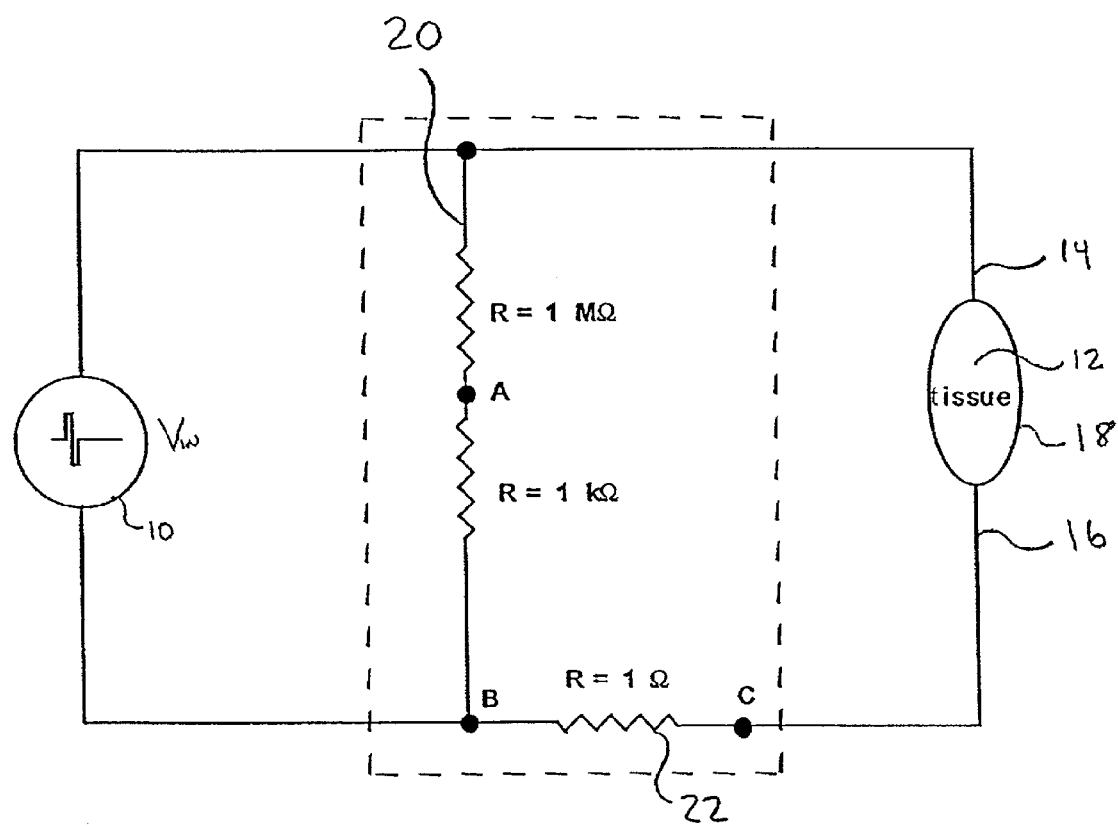
FIG. 1 shows a block diagram of a basic electric stimulation test circuit in accordance with the invention.

The invention comprises methods and devices for testing and for delivery of pharmaceutical agents, and certain pharmaceutical agent formulations, useful for in vivo electrical stimulation treatments of animals and humans to increase the biological efficiency and tolerability of treatments involving nucleic acid and protein formulations. For example, the efficiency with which certain gene therapy and DNA vaccine agents can elicit a robust immune response in biological tissues is enhanced according to the invention, in a manner that renders tolerable a treatment process involving application of electrical energy for iontophoresis, electrophoresis and/or electroporation effects (i.e., electrical stimulation) substantially contemporaneous with infusion of one or more pharmaceutical agents.

The invention comprises several cooperating aspects for in vivo electrical stimulation during treatment with an agent. These include signal generation, signal amplification, electrode structures and configurations and pharmaceutical agent formulations. Additionally there are other aspects of the invention, including, but not limited to, high frequency sampled data sampling and collection using an acquisition system to record various treatment parameters including the applied current and voltage levels at instantaneous sample times. Test data appearing below demonstrate that certain biological effects can be enhanced by electrostimulation during exposure to a pharmaceutical agent, and according to the invention the technique has been refined. Specifically, biological enhancement performance was assessed using conductive electrodes versus partially insulating electrodes versus fully insulating electrodes (at substantially zero current apart from reactive effects, and including trials at the relatively high constant control voltage of ±400V) shows that an inventive electrode arrangement as described herein can achieve the effect of enhancing biological effects using current levels that are limited to an extent that adverse reactions to current, including severe muscular contractions, can be precluded.

The invention relates to the application of Ohms law in either microscopic vector form j=σE, where j=current density vector, σ=conductivity and E=electric field vector; or in macroscopic scalar form V=IZ, where V=voltage, I=current and Z=complex impedance. By using partially insulating electrodes according to the invention, typically coated with a dielectric material having an impedance in the range of 1 KΩ to 10 MΩ, rather than conducting electrodes, (typically of stainless steel with impedances of less than 10 Ω) it is possible, relative to treatment without electrical stimulation, to achieve significant enhancement of biological response. The invention and the partially insulating or dielectric electrodes employed, has the significant advantage of substantially limiting the current applied and flowing in the tissue between the electrodes. This correspondingly limits the level of power applied. However it has been discovered that the level of power can be sufficient to achieve an enhanced desired biological response using a moderate voltage and severely limited current levels, provided a minimal current level is obtained. The technique has the benefit of reducing involuntary muscle contraction due to application of current, and the potential patient or host discomfort associated therewith.

In a preferred embodiment, the invention concerns a method for assessing the performance of a system for delivering a pharmaceutical agent to a portion of a body of a host. The term "pharmaceutical agent" as recited herein encompasses medications, vaccinations and other chemical compounds and formulations, especially including nucleic acid and protein formulations for use in gene therapy and DNA vaccine applications. The term "performance" as recited herein encompasses system efficacy (e.g., favorable immune system response or gene expression level for gene therapy) as well as safety, tolerability as well as any adverse effects. The term "infuse" as recited herein encompasses not only injection but other subcutaneous, transcutaneous, intravenous and oral application or delivery of pharmaceutical agents that are suffused through at least the targeted tissues of the host.

In general, an electrode is applied adjacent to a portion of the body, such as a section of muscle tissue, the electrode being electrically drivable relative to a second electrode placed in another location, such as a similarly structured electrode disposed immediately opposite the muscle or other tissue from the first electrode. A pharmaceutical agent is injected or otherwise infused into the portion of the body, directly or indirectly into the space between the electrodes (e.g., systemically). A signal generator is coupled to the electrodes so as to deliver an at least partially periodic signal across and electrically stimulating the portion of the body. A data acquisition system is used to measure and record the voltage and current delivered, thereby generating electrical parameter data that is collected for reference. The host immune response or gene expression level is measured, for example by periodic assay for the presence of the products or results of immune reactions occurring in response to the pharmaceutical agent. The parameter data and the response data can be subjected to various forms of numerical analysis, but at least part of the parameter data and data characterizing the immune system response are correlated, whereby the performance of the system and of the pharmaceutical can be assessed.

FIG. 1 shows a block diagram of a basic electrical stimulation test circuit according to an embodiment of the invention. In general a signal generator 10 is coupled to a portion of a body of a host 12 (tissue) via an electrode having two needles 14 and 16 (schematically shown) spaced apart and defining a reaction volume 18 between them. A voltage divider 20 is coupled in parallel across the electrode. A 1 Ω current sensing series resistor 22 is coupled in line with the electrode. Various electrode configurations and arrays are compatible with the invention as discussed in more detail below.

Signal generator 10 is preferably an arbitrary waveform signal generator which allows voltage signals of any shape in time, at least among a plurality of selectable wave shapes, to be generated either once or continuously at a selected duty cycle and/or pulse repetition rate. Various waveform shapes are acceptable for use in accordance with the invention and may be particularly apt for certain pharmaceuticals. The waveform shapes may include but are not limited to square, sine, parabola, sawtooth, triangle, exponential rising-falling spikes, uniform noise, negative ramps, sinusoidal sweeps or variations of frequency (chirps) that are logarithmic or linear, and various other such forms. However, it has been discovered that continuous sine waves at about 400 Hz are well tolerated by non-human primates and can be effective in treatments for enhancing gene expression and immune response.

Signal generator 10 includes a signal amplifier comprising a gain adjustable operational amplifier with a feedback arrangement that can be configured to control for constant current ("CC") or constant voltage ("CV") feedback. In a preferred embodiment the control included a constant high voltage ("CHV") mode for control in the range of several hundred volts. This feedback generally seeks to maintain an average constant current or voltage by filtering an instantaneous sense signal and applying the filtered sense signal to a gain control. The electrical characteristics of the tissue being treated may vary somewhat in time (generally, the resistance of tissue is observed to fall during treatment). In operation as a constant current amplifier, signal generator 10 decreases the voltage output level if the average current increases above a predetermined value, thus tending to increase the current level back to the predetermined value, for example a targeted control value. Signal generator 10 likewise can increase the voltage of the output if necessary to obtain a targeted average current. In operation as a constant voltage amplifier, the signal generator 10 will maintain its voltage output even if the loading (the resistance of the tissue between the electrode) varies. Thus the constant voltage amplifier will increase or decrease its output to adapt to changes in current loading. In constant current mode the amplifier could increase the output voltage beyond limits if there was no electrical path between the electrodes (for example if the electrodes are out of contact with the tissue), and in the constant voltage mode the amplifier could attempt to supply unlimited current if the tissue impedance dropped substantially or the electrodes were inadvertently shorted. However the amplifier preferably has output limits in either feedback mode and will peg and thereby limit the range of feedback control to prevent damage.

Signal generators (comprising arbitrary waveform signal generators and operational amplifiers) suitable for use in accordance with the invention are available from various sources. Examples include commercial sources such as FHC, Inc. (Bowdoinham, Me.), National Instruments (Austin, Tex.) and custom sources such as Merck Research Labs RY-Bioelectronics Laboratory, which are particularly suitable.

The voltage applied to the tissue 12 appears across voltage divider 20 as shown in FIG. 1. The voltage across the lower leg of the voltage divider $V_{ab}$ is easily derived from the input voltage ($V_{ab}=V_{in}*1$ K/(1 K+1 M) or $V_{ab}\cong 0.001*V_{in}$). Voltage divider 20 provides a voltage signal across points A and B which is reduced approximately by a factor of $10^3$ with respect to the source voltage $V_{in}$. Aside from reducing the measured voltage across points A and B to a level appropriately scaled for input to a data collection monitor or sampling apparatus, voltage divider 20 causes minimal circuit loading since its total series resistance is negligible with respect to the impedance of the tissue 12 (typically in the range of 200–1000 Ω depending on the input signal frequency).

The current through the tissue 12 is derived from the voltage across 1 Ω series resistor 22. Under Ohm's Law, V=IR, the measured voltage across points B and C is proportional to the current through the 1 Ω series resistor 22 as well as the tissue 18.

Figure 2:
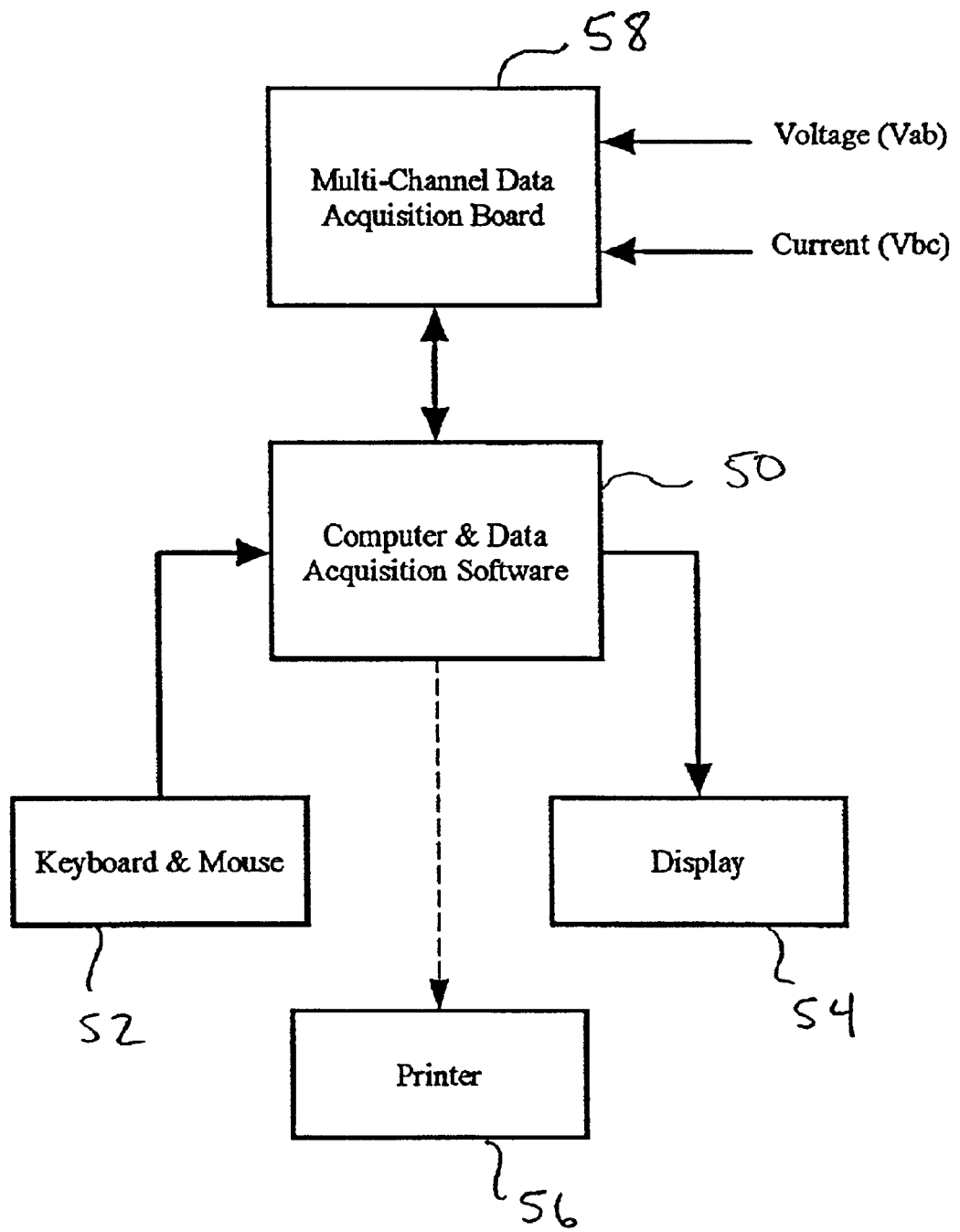
FIG. 2 is a block diagram of a data acquisition system in accordance with the invention.

FIG. 2 shows a data acquisition system for use in accordance with the invention. The data acquisition system comprises a computer or processor and associated data acquisition software 50. Input/output devices for the convenience of an operator include a keyboard and mouse 52, and output devices such as a display 54 and printer 56. The numerical data is input using a multi-channel data acquisition board 58, preferably having high impedance inputs, analog to digital converters, scaling controls to set an input range to correspond to a predetermined range of output values for each input, and one or more timing controllers to determine the rate at which data samples are collected (or possibly to trigger or be triggered by events). A standard PC is acceptable for use as the computer or processor in accordance with the invention, such as a typical IBM compatible PC, Apple compatible, workstation or the like which are available from a variety of sources such as IBM, Hewlett Packard, Compaq, Dell, Gateway and others known to those in the art.

Data acquisition software and multi-channel data acquisition hardware are available from several sources and most typically are used to collect process control data. Models suitable for use according to the invention are available, for example, from National Instruments Corporation of Austin, Tex. For example, according to a practical configuration, acceptable results were obtained with a data acquisition system implemented with the following components (largely available from National Instruments):

AT-MIO-16 E-series Multifunction I/O Data Acquisition (DAQ) Board

LabView Software/NI-DAQ, Windows Full Development System (v5.1)

SCB-68 Shielded I/O Connector Block 68-pin shielded cable

The AT-MIO-16E-1 generally has the following characteristics:

analog inputs: 8-channel differential 12-bit successive approximation Analog to Digital Converter 1.25 Msamples/sec guaranteed, 500 Ksamples/sec stream direct to hard disk The LabView Software controlling the DAQ Board preferably has the following characteristics:

multi-channel recording of independent scale signals

Figure 3:
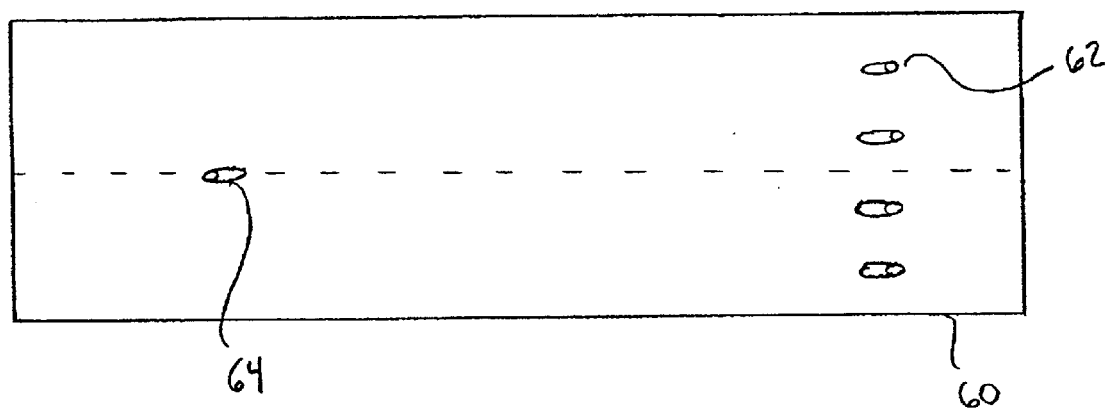
FIG. 3 is a plan view of a needle/electrode holder in accordance with the invention.
Figure 4:
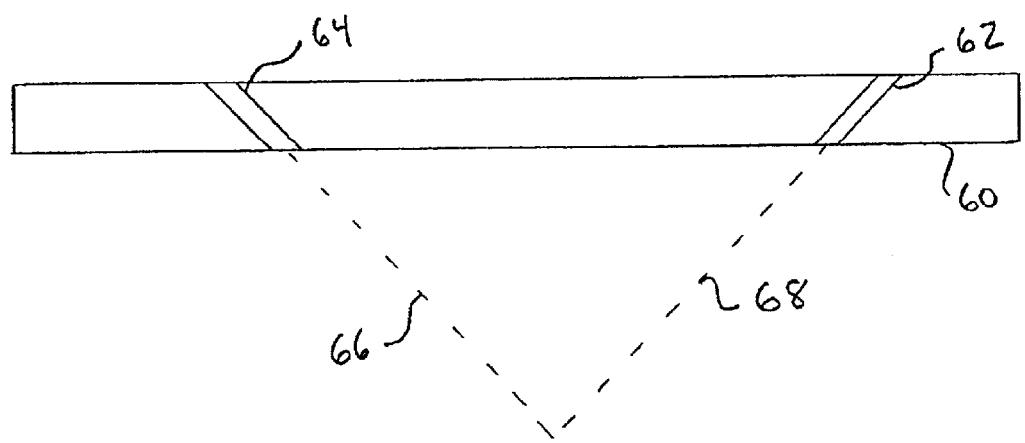
FIG. 4 is a side sectional view of a needle/electrode holder in accordance with the invention.

100 K Scans/sec of 5 channels, each channel measurement separated by 1 μsec data memory buffer: 1,024,000 Bytes scans/write 200 K FIGS. 3 and 4 show a needle/electrode holder 60 in accordance with the invention. The needle/electrode holder 60 generally comprises an electrical insulator such as plexiglass, a polycarbonate or the like as a support and is operable to guide and/or orient both a cannula or hollow needle for infusion of a pharmaceutical agent and a pair of needles for electrical stimulation of tissue, which can be solid rather than hollow and define electrodes that are embedded by insertion in the area adjacent to the treatment area. A preferred needle/electrode holder 60 is approximately 38 mm long, 19 mm wide, 3.2 mm thick and is formed with a plurality of angular guide holes for guiding the needle and electrodes into the proper orientation with respect to the tissue. It is understood that various configurations of needle/electrode holders are compatible with the invention. Electrode guide holes 62 are generally spaced 2 mm apart and are disposed at approximately 30° with respect to the plane of the needle/electrode holder. A single needle guide hole 64 is spaced apart from the electrode guide holes 62 by about 30 mm and is disposed at approximately 40° with respect to the plane of the needle/electrode holder.

The configuration of needle/electrode holder 60 is advantageous for several reasons. Needle/electrode holder 60 controls treatment conditions (i.e., needle orientation and relationship to the reaction area) and ensures that these conditions and can be repeated consistently. It has also been determined that partially insulated electrodes are desirable for use in accordance with the invention. Thus, it is preferable to separately provide an injecting needle for infusing the tissue with a pharmaceutical agent.

The electrodes preferably comprise a conducting material such as stainless steel, uniformly coated with a partially conducting dielectric compound. A shown in FIG. 4, the needle/electrode holder properly orients the injecting needle 66 with respect to the electrodes (single electrode shown schematically as 68) such that the pharmaceutical agent is delivered directly into the reaction area (i.e., into the space between the electrodes). However, numerous electrode configurations are acceptable for use in accordance with the invention including but not limited to hollow electrodes used for both injecting and electrical stimulation, electrode arrays using two or more electrodes and the like.

Figure 5:
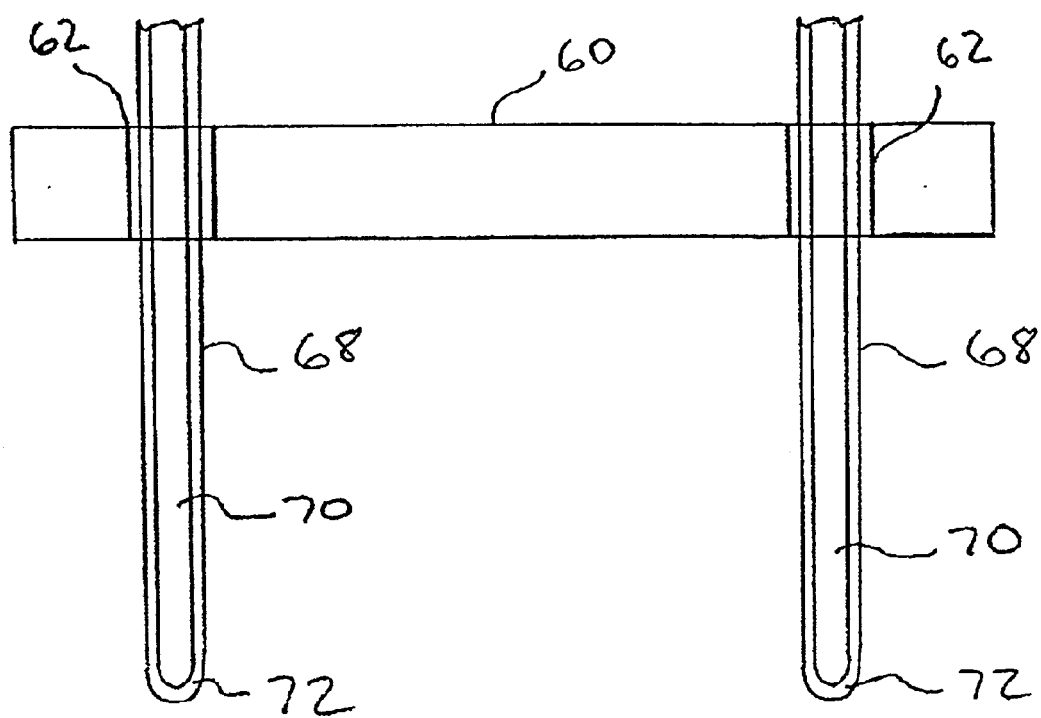
FIG. 5 is a sectional view of a pair of electrodes each having a solid conducting core and a partially conducting dielectric coating carried in a needle/electrode holder in accordance with the invention.

FIG. 5 shows a pair of electrodes 68 carried in the needle/electrode holder 60 (via electrode guide holes 62). Each electrode 68 preferably has a solid conducting core 70 and a partially conducting dielectric coating 72. The solid conducting core 70 is preferably formed from stainless steel or the like. An acceptable thickness is 27 Gauge. Various partially conducting dielectric coatings are compatible with the invention. For example, the electrodes can be coated by airbrush (Testors Corp., Model Master #50603) with PFA such as E.I. Du Pont de Nemours and Co., #420-703, 1700-000; Ryton available from Whitford Corp., West Chester, Pa. Whitford Xylan #1391, 1331 tan, or the like. An alternative is one or more coats of enamel paint (Model Master #1705) and optionally one or more clear top coats (Model Master #2736). In the alternative partially conductive dielectric coatings based on PTFE, PFA, or similar compounds are acceptable from a variety of sources. In general, the dielectric can comprise any durable and unreactive polymer material having limited conductivity or conductivity controlled by the addition of an appropriate portion of conductive particles such as metal powder, carbon black, graphite, etc.

The partially conductive dielectric coating preferably has sufficient dielectric strength to withstand voltage breakdown during electrical stimulation. The partially conductive dielectric coating is also preferably lubricious (i.e., having a low coefficient of friction) so that electrode insertion and removal is facilitated for host comfort. The partially conductive dielectric coating is also preferably suitable for FDA approval as an electrode coating on a medical device. Accordingly, partially conductive dielectric coatings based on PFA compounds are particularly preferable since PFA has a relatively high dielectric strength, is believed to be FDA approved for many applications and is lubricious and abrasion resistant. Inasmuch as PFA is generally an insulator, additional materials such as carbon black or the like can be mixed with PFA prior to coating the electrode. Partially conductive dielectric coatings having an impedance in the range of 1 K$\Omega$ to 10 M$\Omega$ are preferred, although lower and higher resistances, e.g., lower resistances such as 100 $\Omega$, otherwise limited or spatially distributed to obtain a particular configuration of current density, or higher resistances up to 100 M$\Omega$ on the level of the load circuit, are within the present invention.

The electrode coating is sometimes described herein as a partial insulator and sometimes as a partial conductor. The two descriptions are substantially equivalent. In either case, the effect according to the invention is to provide a limitation on the current density through the tissue at the site of treatment while applying a voltage that would produce a substantially higher current under Ohm's law if the electrodes were simply metallic and directly coupled the tissue to the driving signal. It is an aspect of the invention to apply a voltage gradient and to permit current flow through the tissue, but to do so at a relationship between voltage and current that deviates from Ohm's law.

Effectively, the invention contemplates a dielectric barrier wherein charges are bound to render the dielectric nonconductive or an insulator wherein charge carriers are likewise unavailable, while maintaining a minimal current flow. This requires that the dielectric barrier or insulation not be completely effective. Specifically, the dielectric or the insulation can fail to completely isolate the tissue from the metal electrode, for example due to small gaps in the barrier at which conduction is possible. Alternatively, a material that is normally insulating such as a nonconductive (insulating) polymer can be rendered conductive at a resistance controlled by the proportion of conductive particles mixed in when curing the polymer. Suitable conductive particles can be, for example, carbon black, acetylene black, graphite, metallic powder or particles or the like.

According to one embodiment, a nonconductive or dielectric barrier material in the form of an enamel coating was applied to an electrode in the shape of a sharpened cylinder apt to pierce the tissue adjacent to the site of treatment. The electrical insulation of the electrode was less effective than the insulation that would have been expected from the enamel material, and it is believed that the insulation could not provide a sufficiently continuous or durable physical barrier covering over the sharpened point of the cylinder, and thus provided a leaky insulation or barrier effect. Surprisingly, a leaky barrier electrode as described was found to be effective for electrical stimulation, whereas a complete insulation barrier was not effective. Further tests have indicated that an electric field applied across the tissue area can provide effective electrical stimulation according to the invention, provided there is at least minimal current flowing, for example at least several milliamps peak.

The current and voltage conditions established to provide electrical stimulation according to the invention are generally such that a voltage is applied across the tissue sample. Insofar as there is a partially-conductive or partially-insulating barrier defined by a resistive, dielectric or insulating material between the conductive electrodes and the tissue, a portion of the voltage drop between the conductive portions of the electrodes may result in a voltage gradient across the barrier rather than across the tissue subjected to electrical stimulation. However, an electrode arrangement in which a slightly discontinuous dielectric barrier may provide a larger voltage gradient on isolated portions of the tissue without the current density that would result according to Ohm's law if the electrodes were entirely conductive. In short, according to an inventive aspect, the electrical stimulation is applied under voltage and current conditions that do not comport with Ohm's law considering the resistance of the tissue being treated. In particular, the current supplied to the tissue is limited to less than the current that would be produced by the same voltage drop coupled in a more conductive manner to the tissue under stimulation.

The data acquisition system is operable to record and document, at over 100 K samples per second, the electrical parameters and conditions during the entire time course of the electrical stimulation process. The system is capable of streaming data to hard disk at rates of up to 5 M samples per second for up to 4 channels in parallel (e.g. when using a National Instruments PCI-611 bel). Data acquisition systems are available at other specific data rates.

The electrodes are inserted into the tissue, preferably parallel to the muscle fibers. In general, the pharmaceutical agent is injected into the tissue using the needle/electrode holder 60. The electrodes are energized with the desired waveform for a preselected time interval.

According to another aspect of the invention, a plurality of opposed electrodes defining pairs or groups of interleaved electrodes or other configurations can be provided and driven from different signals or structured to have different conductive characteristics such that the tissue is treated by the concurrent effect of currents at particular amplitudes that are provided from coupling between the tissue and different electrodes or electrode surface areas. For example, a first signal generator can be coupled to a pair of conductive electrodes and a second signal generator coupled to a pair of partially conductive electrodes. An injecting needle or cannula, can be positioned to discharge a pharmaceutical into a space between the two pairs of electrodes. Preferably, a needle/electrode holder is provided with a plurality of angular guide holes for guiding the needle and electrodes into the proper orientation with respect to the portion of the body and with respect to the electrodes. The first signal generator is preferably an arbitrary waveform signal generator for generation of signals of selected shape in time and a signal amplifier (for example short pulses at a relatively low voltage for delivering instantaneous peak current of about 15–20 mA). The second signal generator can also be an arbitrary waveform signal generator for generation of signals of selected shape in time and a signal amplifier (for example low frequency sine wave signals at 100 volts for 10 seconds, providing a potential difference but substantially no current flow). Both amplifier outputs are preferably configured in one of a constant current and constant voltage feedback control mode.

SPECIFIC EXAMPLES

Numerous test runs were made in which a portion of the body of a host was electrically stimulated with a time varying signal and the voltage and current delivered to the portion of the body while electrically stimulating the portion of the body were measured and recorded using the data acquisition system disclosed above. During subsequent test runs, a wide range of parameters were varied. In all cases, the efficacy of the delivery of the pharmaceutical agent was explicitly quantified by measuring enhanced gene expression and/or enhanced immunological responses.

Involuntary muscle contraction is a known undesirable side effect resulting from electrical stimulation within certain ranges. In general it has been determined that higher frequency signals (e.g., a 50 KHz sine wave) give rise to less muscle contraction than relatively lower frequency signals (e.g., 400 Hz sine wave) at the same amplitude.

Various waveform shapes were also tested and deemed acceptable for use in accordance with the invention, including but not limited to square, sine, triangle, exponential rising-falling spikes, uniform noise, negative ramps, and logarithmic sinusoidal sweeps and the like.

Figure 14:
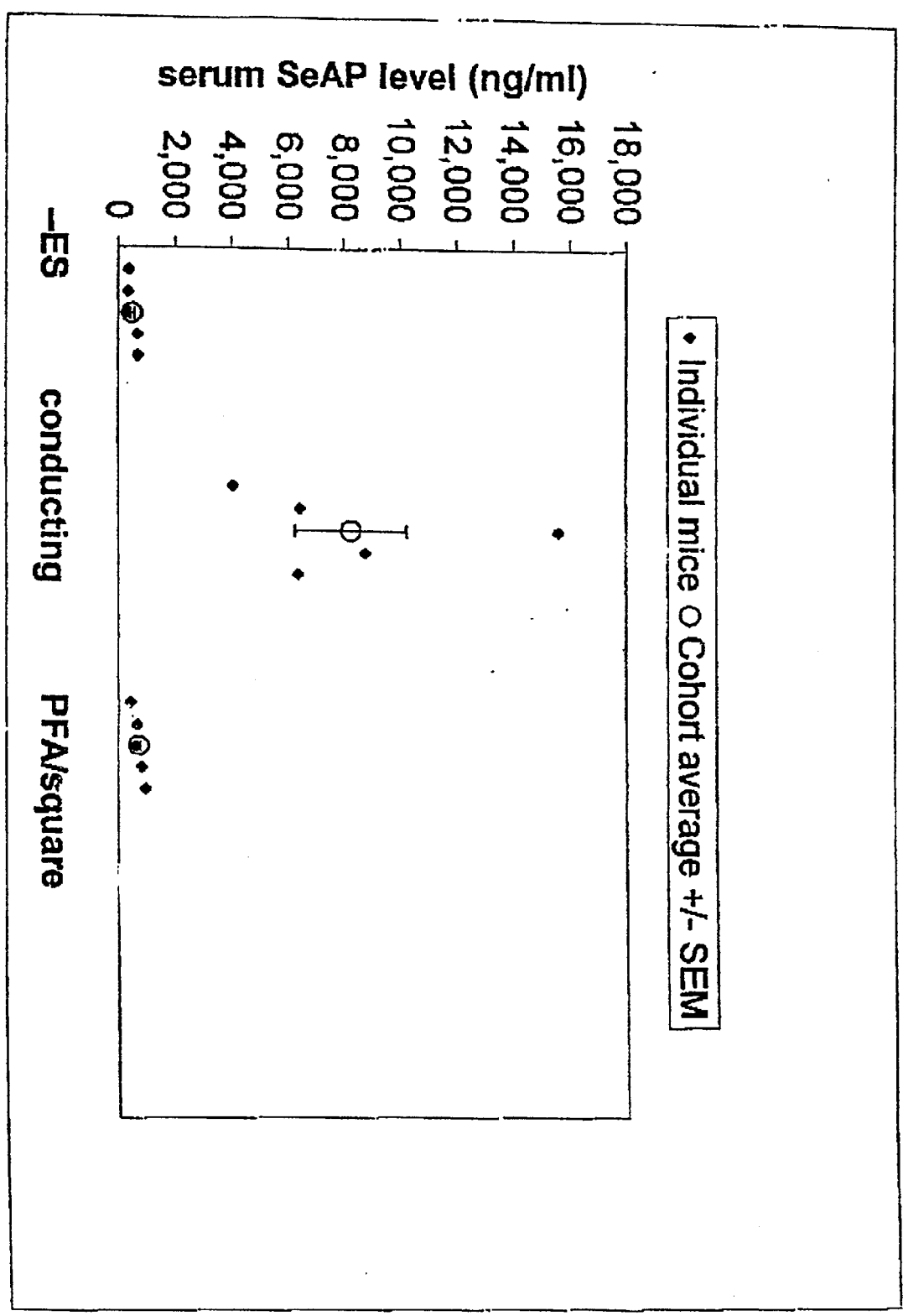
FIG. 14 shows serum SeAP levels in balb/c mice 8 days post injection, which were subjected to (I) no electrostimulation (−ES), (ii) electrostimulation with conducting stainless steel electrodes, and electrostimulation with completely insulating PFA electrodes with (iii) square pulses. Data is presented for individual mice (♦) and cohort average (○), with standard errors of the mean (SEM) indicated.

It has also been determined that as shown in FIG. 14, electrical stimulation carried out with electrodes covered with a non-conductive coating produced no enhancement in the biological response to tested pharmaceutical agents. Electrodes covered with a non-conductive coating of relatively pure PFA had excellent dielectric strength properties, abrasion resistance, lubricity and the like. As expected however, fully insulated electrodes yielded no measurable current during electrical stimulation, as recorded by the data acquisition system. It was determined according to the invention that at least some current flow or charge transfer is required to produce an enhancement in the biological response to tested pharmaceutical agents. It was also determined that increased involuntary muscle contraction is associated with an increase in current flow, particularly with relatively lower frequency signals, but that by limiting the current to remain slightly above a predetermined minimal average current, biological effects could be obtained without the disadvantages of such contractions.

Insofar as muscle contractions occur in the tissue between the electrodes, the tolerability of the contractions can be reduced if the electrodes are closely spaced. For example, the distance between the electrodes can be kept small compared to the extension of the muscle in which the electrodes are placed. Thus reducing the spacing of the electrodes from 8 mm to 4 mm under otherwise identical conditions can reduce the extent of contractions in muscle tissue of mice.

Thus, in correlating all of the data gathered from numerous test runs, applicant determined that electrodes having a conductive body portion that is covered in a leaky dielectric of partially conductive coating provide an enhancement in the biological response while reducing many undesirable side effects. A pair of electrodes each having a leaky dielectric formed of a partially conductive coating were applied to the tissue using a needle/electrode holder as disclosed above. A pharmaceutical agent was injected into the reaction area. The signal generator was configured in a constant voltage mode at approximately 200 volts peak to peak. The signal shape utilized was a square wave having 10 trains of 1000 pulses, each pulse having a 100 volt peak for 200 $\mu$sec, $-100$ volt peak for 200 $\mu$sec and 600 $\mu$sec off.

Figure 6:
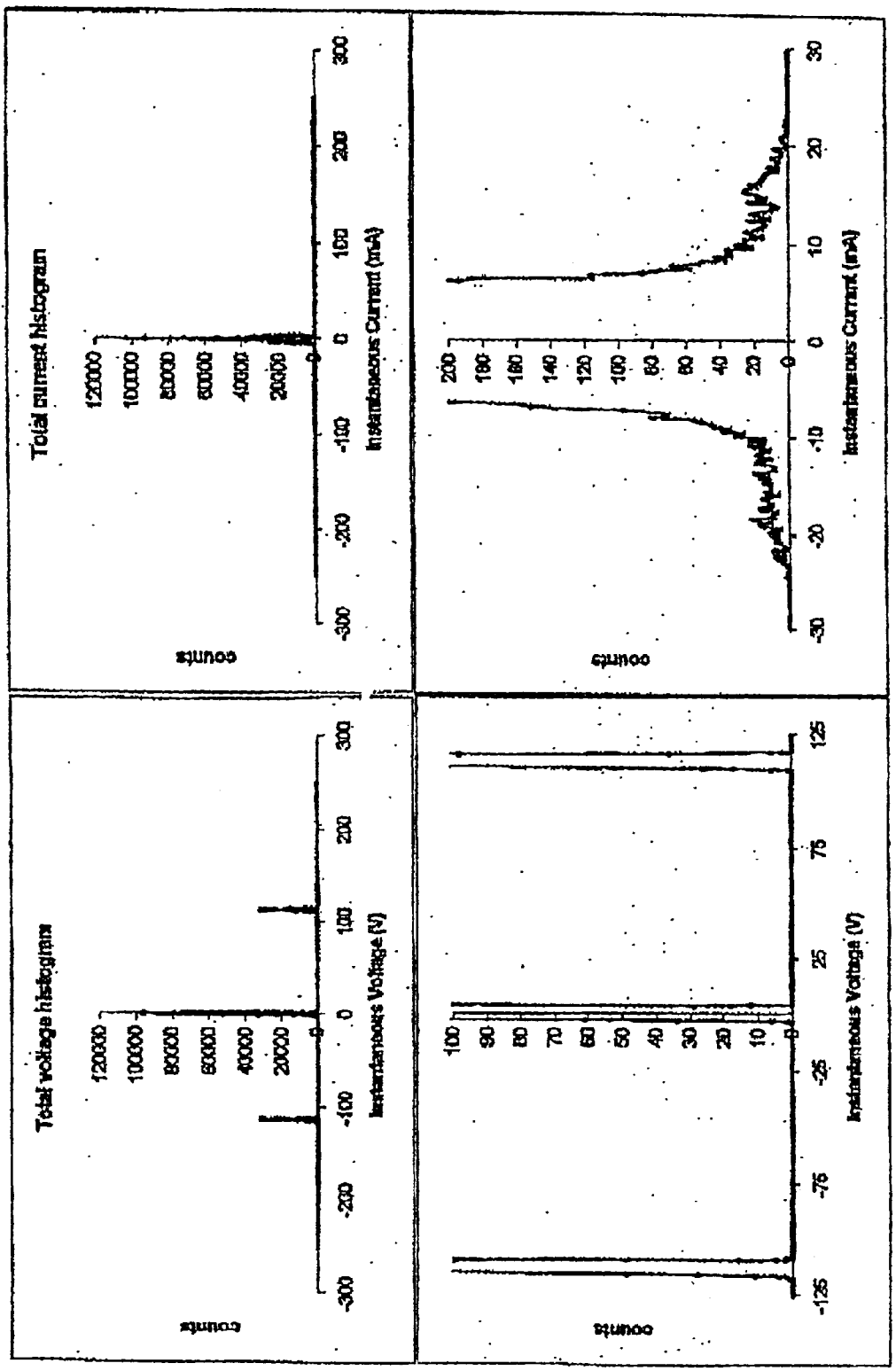
FIG. 6 is an exemplary display from the data acquisition system showing the electrical test data gathered from electrical stimulation using a pair of electrodes each having a solid conducting core and a partially conducting dielectric coating in accordance with the invention.

FIG. 6 shows an exemplary display after post-treatment analysis from the data acquisition system showing the electrical test data gathered from subject electrical stimulation. In general, instantaneous current was less that 20 mA, and (in constant voltage control mode) the current amplitude tended to fall off during each pulse train. Thus, host discomfort due to involuntary muscle contraction was minimized. Under these conditions, the tissue receives a total charge in the range of 5–20 millicoulombs per treatment. However, this charge is delivered rapidly and in the presence of an electric field having a nominal voltage gradient on the order of 330 Volts per cm of electrode separation (100 volts over 3 mm), subject to local tissue density variations.

Advantages of the Invention

Numerous advantages are provided by employing the present invention, a non-exhaustive list is disclosed below. The invention provides a diagnostic tool which enables accurate measurement and recording, with sufficient temporal resolution, of the entire time course of relevant electrical parameters, including minimally, the applied electric field (voltage) and delivered current across electrodes in contact with biological tissue. Measurement and recording of relevant electrical signals enable quantitative analysis of electrically stimulated animal subject records; determining and optimizing the mechanism of action, either: (a) electric-field/voltage (electroporation); (b) current driven (iontophoresis); or (c) another phenomenon; establish and ensure equivalent treatment from subject to subject within a cohort; permit understanding of biological tissue loading of signal generators, to optimize signal generator, electrical signals and electrode configuration; e) allow processes to be "scaled" to treat larger tissue volumes (e.g. human relevant doses of 0.5–1.0 ml injection volume); further understanding of electrical characteristics (conductivity/impedance, reactance/reluctance, frequency response, etc.) of biological tissue; enable correlation studies of electrical signal parameters with non-electrical variables, such as biological efficacy, involuntary muscle contraction, etc; facilitate development of "equivalent circuits" and computer simulations of animal model tissue, for conceptual extension to the human clinic; open the realm of quantitative measurements of involuntary muscle contraction; and provide for documentation of an accurate and complete record of electrical stimulation treatment (and suitable analysis in case of adverse reaction).

Additionally and critically it has been observed that the involuntary muscle contraction observed increases with the current or integrated charge delivered. Also, the apparent tolerability to the electrical stimulation treatment appears to be monotonically related to the current amplitude or total integrated charge. Thus, the present inventor teaches an approach to achieve an enhanced biological response, while attempting to minimize the negative aspects of large current or high total charge delivery.

The invention also relates to improved methods of electrostimulation treatments of skeletal muscle cells and other host tissue to promote in vivo delivery of nucleic acid molecules and other pharmaceutical entities. Additional host tissue which may be subject to electrostimulation includes but is not limited to cardiac muscle, subcutaneous, dermal, tumor, arterial, lung, kidney, liver and ocular tissue, etc.

The amount of expressible DNA to be introduced to a vaccine or gene therapy recipient will depend on the strength of the transcriptional and translational promoters used in the DNA construct, and on the respective immunogenicity or therapeutic value of the expressed gene product. Synthetic DNA vaccines and gene therapy expression cassettes are known in the art and may be provided in various forms so as to promote optimal expression of the transgene. The DNA vaccines will provide effective immunoprophylaxis or therapeutic intervention against viral or bacterial infection through neutralizing antibody and/or cell-mediated immunity. In general, an immunologically effective dose for either prophylactic or therapeutic (vaccine or gene therapy applications) of about 1 µg to 10 mg, and preferably about 1 mg to about 5 mg of plasmid DNA is administered directly into human muscle tissue in conjunction with the electrostimulation as described herein. Although direct injection of skeletal muscle is a preferred route of administration either by needle or needle-less jet injection, other routes which are amenable to the electrostimulation methodology described herein include but are not limited to subcutaneous injection/ electrostinulation, intradermal introduction/ electrostimulation, etc. Impression through the skin and intraperitoneal administration with electrostimulation are also contemplated.

One embodiment of the present invention relates to utilization of this methodology for delivery to skeletal muscle of a DNA molecule which expresses a gene(s) of interest for applications such as DNA vaccine technology or gene therapy applications. This portion of the invention relates to direct injection of a nucleic acid into skeletal muscle accompanied by electrostimulation of the muscle within the vicinity of the injection site utilizing a set of partially conducting electrodes or 2 sets of complementary electrodes as described herein. A voltage is applied across these electrodes to generate an electric field, in view of the type of electrode utilized, results in a voltage/current relationship wherein the volumetric current density is less that the current density that could be obtained under Ohm's Law using direct conductive contact between the opposed electrodes and the tissue. Specifically, instead of a relationship between applied voltage and electrode current equal to the resistance of the tissue, a lower current obtained by interspersing series resistance, or preferably by reducing the points of contact with the tissue using a discontinuous resistive, dielectric or insulating barrier whereby the contact and greatest current density occurs at isolated locations. Application of current in conjunction with a voltage in this manner results in an increase in the delivery and/or expression of DNA expression plasmids to host tissue while also substantially minimizing or completely eliminating involuntary muscle movements, perhaps by substantially confining the current density to isolated pathways representing a relatively small proportion of the bulk of the tissue at the treatment site. These involuntary muscle movements are associated with the application of a voltage driven current across a tissue with conducting electrodes (e.g., stainless steel) wherein the bulk of the tissue is subjected to the voltage gradient and current density. This reduced current and total delivered charge result in minimal or no involuntary muscle contraction in combination with enhanced delivery of the pharmaceutical entity to the host compared to no electrostimulation. The electrostimulation procedure disclosed herein results in enhanced biological response or cellular transfection of a pharmaceutical agent to the host, including but not limited to mammalian hosts such as a non-human primate or a human host, without deleterious side effects such as pronounced involuntary muscle reflexes known to be associated with application of higher currents.

When using partially conducting electrodes of the present invention, where the high impedance of the dielectric coating prevents a large current flow but allows an electric field to penetrate between the electrodes, a constant voltage (CV) feedback configuration of the signal amplifier is preferred in order to regulate the amount of potential placed between the two polarities of the electrodes. By using partially insulating or 2 sets of complementary electrodes as described within the specification, it is possible, relative to treatment without electrical stimulation, to achieve significant enhancements in biological response using the methods and devices of the present invention. Moreover, the present invention (utilizing partially insulating or 2 sets of complementary electrodes) has the significant advantage of reducing the current applied to the host during the treatment process and thus the amount of involuntary muscle contraction and perhaps pain associated therewith. It will be known upon review of this specification that arrays of multiple electrodes may be utilized near a single administration site, or possibly at multiple sites of administration.

Figure 7:
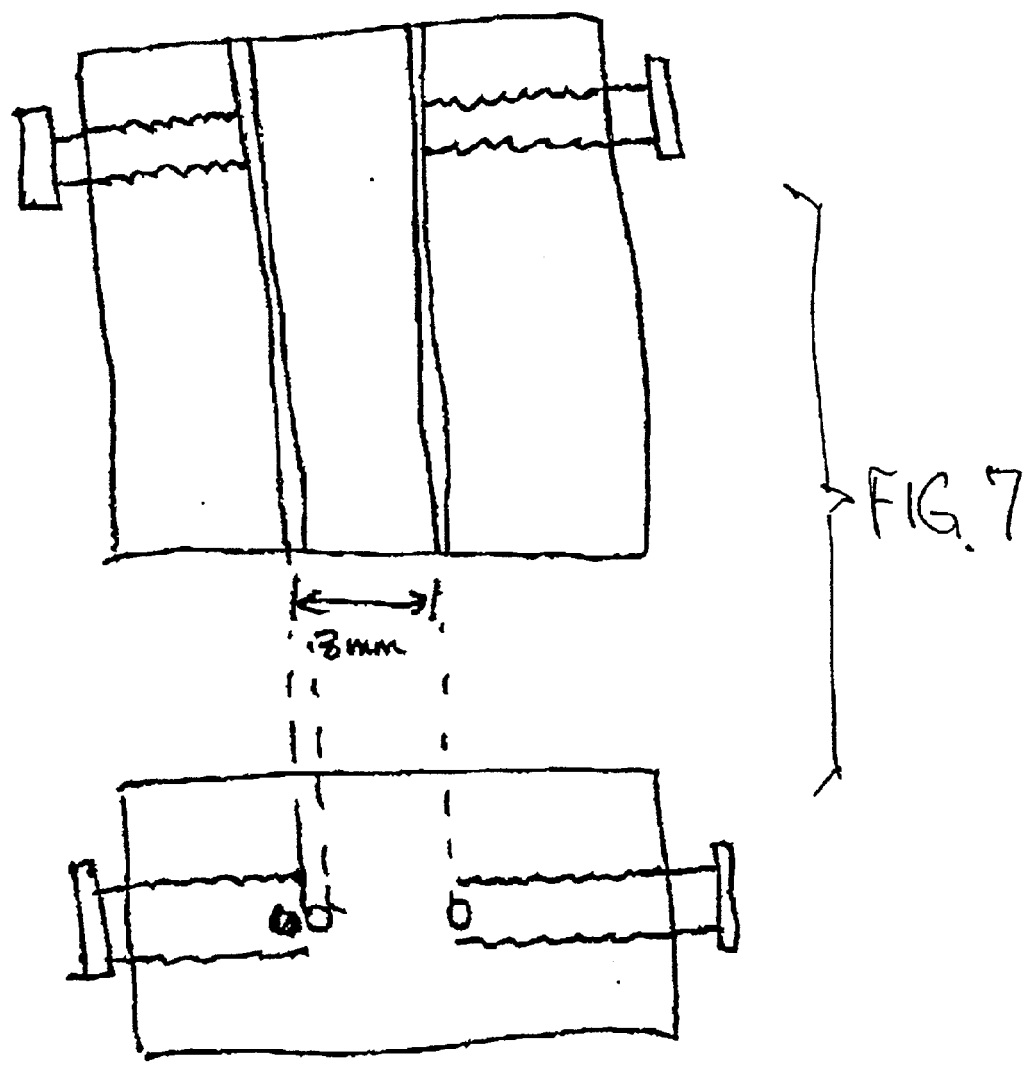
FIG. 7 is a section view of an alternate electrode holder in accordance with the invention.
Figure 6:
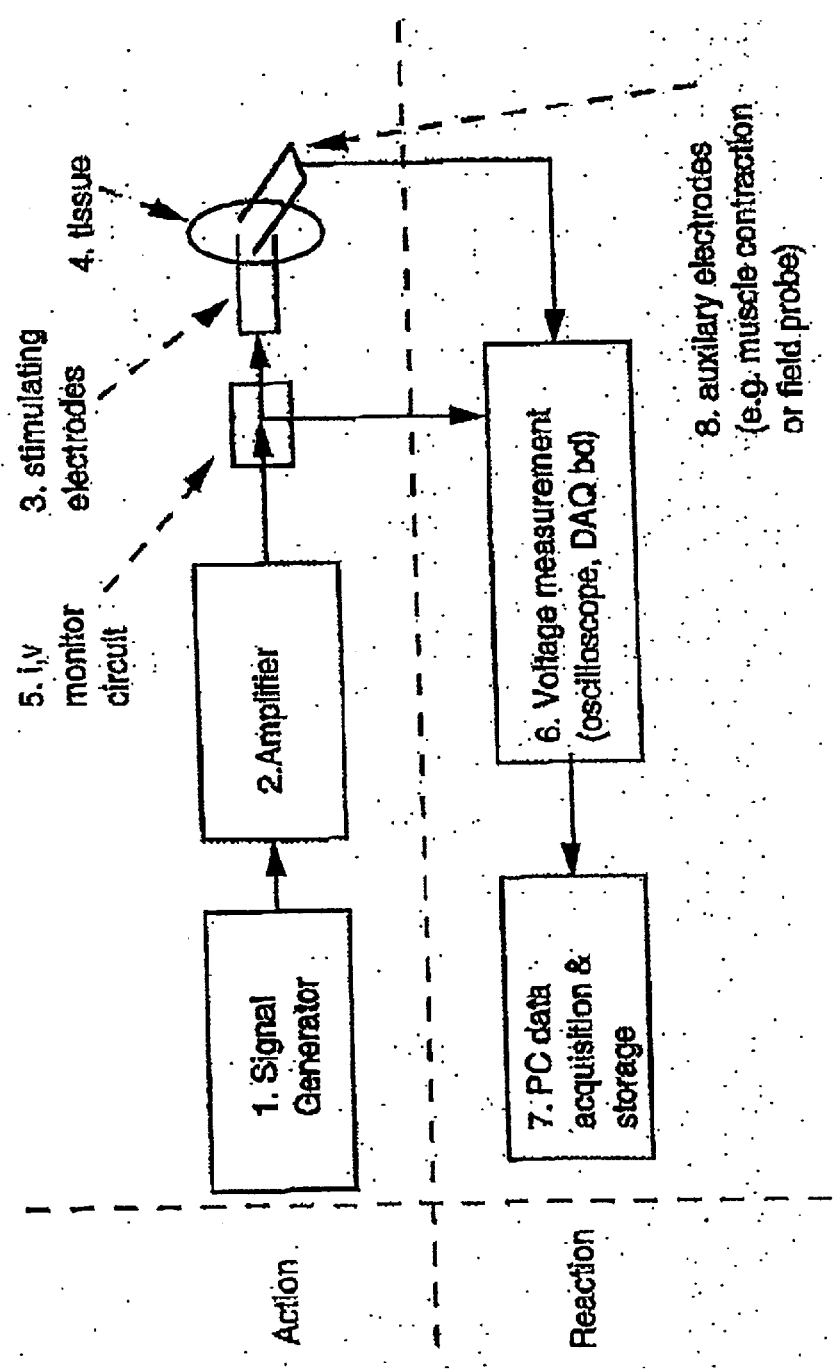

As shown in FIG. 3, a specific embodiment involves use of plexiglass needle/electrode holder to better align the needles and electrode with the target tissue. The angle of entry for the needle and electrodes as well as the distance between the electrodes as shown in FIG. 3 is not critical. An alternative embodiment of electrode holder, substantially comprising a block of insulating material such as polycarbonate, with bores for slidably holding elongated electrodes and set screws for adjusting the protruding length of the electrodes, is shown in FIG. 7, particularly as adapted for treatments in mice. The distance between the electrodes may be from a fraction of a mm to about 10 mm, with the data mentioned herein being developed using such a mounting of electrodes spaced at a range from about 1 mm to about 4 mm.

The time of infusion of the pharmaceutical entity in relation to application of the electrical stimulus is not overly critical, as long as electrostimulation takes place after the infusion or needle injection, and while the entity remains at an effective concentration in the tissues treated. Others have shown that electrostimulation treatment before infusion of the pharmaceutical agent does not produce desired enhancements in biological response, and the treatment obviously cannot proceed with the benefit of a pharmaceutical if the pharmaceutical is no longer present in the tissue.

The core of this portion of the invention, and as shown in the Example section, is the ability to apply a constant voltage through partially insulating or 2 sets of complementary electrodes such that a relatively modest current flows in the presence of a non-Ohmic electric field within the tissue. This reduced current is coupled with a relatively low total charge transferred across the tissue during the time course of the treatment. This results in a significant reduction or disappearance of the involuntary muscle reflexes mentioned above and in turn makes this methodology very appealing in the clinical setting. The high speed data acquisition system described herein creates a digital record of both applied voltage and current measurements, which allows calculation of the treatment variables like the total charge transferred during that specific treatment. It is shown in the Example section that the methodology of the present invention delivers approximately a 5 to 30 fold reduction in total charge while still enhancing transfection of target muscle cells and, in the case of delivering a DNA plasmid expression construct, resulting in significantly increased levels of transgene expression as compared to injection without electrostimulation.

It will be evident upon review of this specification that the selection of electrical signals, amplifier mode, electrodes and infusion formulation are inter-related in many well know ways. Several considerations include but are not limited to:

(1) Ohms law must generally be obeyed as with any conducting circuits, as well as the AC Poisson equation for potentials in the quasi-static domain below 1 MHZ; however it is appropriate to consider the effect of these relationships on both the level of the electrodes generally and the smaller scale of discrete electrode surface areas, discrete tissue structures and the like.

(2) The electrical signals are characterized by frequency, amplitude, spectral decomposition (e.g. Fourier power spectrum), shape, cadence, etc. Variations and changes in these must likewise obey the laws of physics.

(3) To the same end, an electric field E scales dimensionally proportional to the potential difference V established and inversely proportional to the distance D separating the potentials. Thus changes or differences in both voltage and distance as well as other aspects of geometry must be assessed. Insofar as the tissue is presumed to function as a resistance between the electrodes, it should be recognized that the application of electrical energy and joule heating can alter the conductive nature of the tissues and/or the coupling between the tissues and the electrodes over time.

(4) A current I is the time rate of change of charge (i.e., the first time derivative of charge) and thus changes in the time of treatment must be assessed;

(5) The current density j is the total current I divided by the cross sectional area A over which the current is spread. However, the host tissue in which the current is propagating is neither spatially isotropic nor homogeneous (for instance skeletal muscle fibers run uni-axially), thus one must consider not only the spatial extent or area over which the current would distribute itself, but also factor in the nature and orientation of the treatment electrodes to both the macroscopic anatomy as well as the microscopic structure of the host tissue under treatment;

(6) Electronic devices can be designed with various specific driving elements, such as one shot charging/dissipative devices (e.g., coils or capacitors), switching elements that couple voltage or current momentarily and other known techniques, and can be controlled by reference devices, or by feedback configurations, the specific embodiments discussed being nonlimiting examples.

An operational amplifier is an exemplary device for generating electrical signals suitable for electrostimulation, and can be readily coupled in a feedback control arrangement so as to maintain control of the output of a driving amplifier based on voltage, current or other measures (e.g., wattage). Thus for partially or completely insulating electrodes, primary use of a constant voltage (CV) feedback configuration is recommended, whereas for 2 sets of complementary electrodes, a constant current (CC) configuration is advantageous for use with the complementary conducting set of electrodes.

(7) Conducting electrode materials as discussed are presumed to be low resistance metals having an internal resistance that can substantially be ignored. However, stainless steel is preferred and in various formulations of stainless steel the conductivity/resistivity of the material can vary and alter the charge injection.

(8) Properties of the dielectric coated electrodes (either partially or completely insulating) must be accounted for. For instance dielectric strength, dielectric constant, microporosity, and lubricity are important factors according to the invention.

(9) Adjuvants (like aluminum salts) included in the infusion formulations can alter the spatial impedance of the tissue under treatment.

General adjustment and adaptation of these parameters are possible and will be apparent to one of skill in the art, and within the scope of the present invention, in view of the foregoing discussion and the following discussion of examples.

According to an important aspect of the invention, voltage to the tissue is coupled through a set of partially insulating electrodes or two or more complementary sets of electrodes, and across a treatment area whereby a current is applied to the tissue in the presence of an electric field; however the relationship is not strictly one of voltage on the electrodes producing a current in the tissue based on the tissue resistance. It in shown herein that the current at any given time may vary during the treatment but that the disclosed method of electrostimulation is based in part on delivering an instantaneous current density on the order of less than 20 mA through a tissue volume of 0.09 $cm^3$. In the examples discussed, the treatment volume was approximately 0.3× 0.3×1.0 $cm^3$, which was found to reduce or completely abolish involuntary muscle reflexes. However, the current density at least proceeding from local sites of conduction on the surfaces of the electrodes, was sufficient to obtain the biological enhancement effects sought.

It is also an important aspect of the invention that the electrostimulation can be conducted over a time course that may range from microseconds ($\mu S$) up to about 1 hour. A prolonged electrostimulation procedure (similar to an ultrasound therapy of muscle tissue which can be 20 minutes per muscle for athletes) is contemplated with the disclosed methodology due to the reduced current applied to the tissue as well as the reduction or abolishment of involuntary muscle reflex.

Any useful waveform may be applied during electrical stimulation of the muscle tissue which results in increased transfection of the pharmaceutical entity. For example, the application of an alternating current may include, but is not limited to, unipolar or bipolar sine waves as well as nonsinusoidal waveforms such as triangle waveforms, square waveforms, exponential rising-falling waveforms, uniform noise, negative ramps, and logarithmic sinusoidal sweeps.

The disclosed apparatus and methodology may be utilized to deliver one or more entities which include but are not limited to nucleic acid molecules, proteins, antibodies, virus particles (such as recombinant viruses, inactivated or attenuated viruses), virus-like particles (VLPs), polymers, formulated nucleic acids (such as PLGA microspheres, cationic lipids [such as DMRIE:DOPE]) which may show adjuvant properties), as well as small organic or inorganic molecules which have acceptable pharmaceutical profiles. The pharmaceutical entity may also be associated with liposomes, such as lecithin liposomes or other liposomes known in the art, as a DNA-liposome mixture (see, for example, WO93/24640). The pharmaceutical entities, especially DNA plasmid expression vectors, may be formulated with an adjuvant or adjuvants which may increase immunogenicity of the DNA polynucleotide vaccines of the present invention. A number of these adjuvants are known in the art and are available for use in a DNA vaccine, including but not limited to particle bombardment using DNA-coated gold beads, needle-less jet injection of DNA vaccines, co-administration of DNA vaccines with plasmid DNA expressing cytokines, chemokines, or costimulatory molecules, formulation of DNA with cationic lipids or with experimental adjuvants such as saponin, monophosphoryl lipid A, OPTIVAX polymers, or other compounds which increase immunogenicity of the DNA vaccine. Another adjuvant for use in the DNA vector vaccines of the present invention are one or more forms of an aluminum phosphate-based adjuvant wherein the aluminum phosphate-based adjuvant possesses a molar $PO_4/Al$ ratio of approximately 0.9. An additional mineral-based adjuvant may be generated from one or more forms of a calcium phosphate. These mineral-based adjuvants are useful in increasing humoral responses to DNA vaccination without imparting a negative effect on an appropriate cellular immune response. These mineral-based compounds for use as DNA vaccines adjuvants are disclosed in PCT International Application No. PCT/US98/02414, PCT International Publication No. WO 98/35562, which is hereby incorporated by reference. One such aluminum phosphate adjuvant is available under the trade name Adjuphos®. Additional aluminum based adjuvants include aluminum hydroxide (such as Allhydrogel®).

Any nucleic acid of interest is a candidate for this methodology, including but not limited to DNA, such as closed circular or linearized plasmid DNA, oligonucleotides, cDNA molecules or genomic DNA fragments amenable to transfer into muscle cells. In addition, delivery of RNA molecules is encompassed within the present invention. As exemplified herein, a particularly useful application relates to enhanced delivery and transfection of a DNA plasmid expression vector to skeletal muscle cells. This electrostimulation-enhanced increase in transfection efficiency in skeletal muscle cells logically results in increased expression of the antigen(s) of interest. Thus the invention can improve the immune response associated with delivery of a DNA vaccine and can ameliorate disease or disorders subject to various gene therapy applications.

The DNA plasmid vectors disclosed herein are known in the art. It will be evident to the artisan of ordinary skill that while the V1Jns vector described herein is used to exemplify the improved methodology, that other vectors described herein, as well as comparable DNA expression vectors may be utilized to practice the invention. Preparation of the vaccine vectors V1, V1J, V1Jneo, V1Jns, V1R is described in WO94/21797 (PCT/US94/02751), which is hereby incorporated by reference. In addition, it will be useful to utilize DNA plasmid vectors which comprise appropriate leader sequences, such as but not limited to a tPA leader sequence. Examples of such DNA plasmid expression vectors comprising the above-mentioned vector backbones are disclosed in WO97/31115 (PCT/US97/02294), which also shows the effect of utilizing codons optimized for expression in the target host, such as a human host. The WO97/31115 specification is also incorporated by reference.

Examples of viral or bacterial challenges which may be amenable to either a prophylactic or therapeutic treatment include but are not limited to human immunodeficiency virus (HIV), herpes simplex virus (HSV), influenza, tuberculosis, human papilloma virus, hepatitis A, hepatitis B, and hepatitis C. It will also be within the scope of the present invention to provide prophylactic or therapeutic treatment for non-infectious diseases, such as cancers, autoimmune disorders, and various allergies by utilizing the components of the invention described herein. This approach to vaccination is applicable to tumors as well as infectious agents, since the CD8 CTL response is important for both pathophysiological processes. Any such DNA vaccine formulation may be delivered by the components and methodology of the present invention, and may also be useful for any number of veterinary applications, including but not limited to rabies, distemper, foot and mouth disease, anthrax, bovine herpes simplex and bovine tuberculosis.

A preferred DNA vaccine is an HIV-based vaccine, including but not limited to a an HIV DNA vaccine which expresses an antigen which represent whole or portions of the coding region of various HIV genes, including the structural genes of gag (p55, or portions thereof, such as p17, p24, p9, p6, or further epitopes thereof), pol (such as the entire coding regions, regions which encode specific activities, such as protease, reverse transcriptase activity, RNase activity, and/or integrase activity, or portions thereof) and env (such as gp160, gp41 and/or gp120, and portions thereof), HIV accessory genes, such as nef, Vpu, Vif, Vpr and/or Vpx, or portions thereof, and HIV transactivation genes such as tat and rev, or portions thereof. A specific HIV-1 based DNA vaccine construction is one which comprises a V1Jns backbone fused to a nucleotide sequence which encodes the p55 gag antigen, wherein the codons within the open reading frame have been optimized for expression in humans. This construct is referred to as V1Jns-FLgag. The open reading frame for V1Jns-FLgag, which encodes HIV-1 p55 gag, wherein codons have been optimized for expression in humans, is shown within WO 98/34640 (PCT International Application No. PCT/US98/02293). The initiating methionine (ATG codon) is represented by nucleotides 10–12 and the "TAA" stop codon runs from nucleotides 1510–1512 of a representative HIV-1 p55 gag antigen. The synthetic gene segments for increased gag gene expression were converted to sequences having identical translated sequences but with alternative codon usage as defined by R. Lathe in a research article from *J. Molec. Biol.* Vol. 183, pp. 1–12 (1985) entitled "Synthetic Oligonucleotide Probes Deduced from Amino Acid Sequence Data: Theoretical and Practical Considerations". The methodology described below to increase of expression of HIV gag gene segments was based on our hypothesis that the known inability to express this gene efficiently in mammalian cells is a consequence of the overall transcript composition. Thus, using alternative codons encoding the same protein sequence may remove the constraints on expression of gag. The specific codon replacement method employed may be described as follows: (1) identify placement of codons for proper open reading frame; (2) compare wild type codon for observed frequency of use by human genes; (3) if codon is not the most commonly employed, replace it with an optimal codon for high expression in human cells; (4) repeat this procedure until the entire gene segment has been replaced; (5) inspect new gene sequence for undesired sequences generated by these codon replacements (e.g., "ATTTA" sequences, inadvertent creation of intron splice recognition sites, unwanted restriction enzyme sites, etc.) and substitute codons that eliminate these sequences; and, (6) assemble synthetic gene segments and test for improved expression.

These methods were used to create the following synthetic gene segments for HIV gag creating a gene comprised entirely of optimal codon usage for expression. While the above procedure provides a summary of our methodology for designing codon-optimized genes for DNA vaccines, it is understood by one skilled in the art that similar vaccine efficacy or increased expression of genes may be achieved by minor variations in the procedure or by minor variations in the sequence.

The following examples are provided to illustrate the present invention without, however, limiting the same hereto.

Example 1

Effect of Electrostimulation at Constant Voltage and Low Current on Gene Expression Materials—*E. coli* DH5(strain, penicillin, streptomycin, and ultrapure CsCl were obtained from Gibco/BRL (Grand Island, N.Y.). Kanamycin and phytohemaglutinin (PHA-M) were obtained from Sigma (St. Louis, Mo.). The secreted alkaline phosphate gene was purchased from Tropix (Bedford, Mass.) and cloned into V1JnS following standard procedures.

Plasmid Preparation—*E. coli* DH5α cells expressing the SeAP plasmids were grown to saturation in LB supplemented with 100 $\mu$g/mL kanamycin. Plasmid were purified by standard CsCl method and solubilized in saline at concentrations greater than 5 mg/mL until further use. All preps were stored frozen at −20° C. until diluted for use. DNA was formulated minimally in normal saline or PBS, diluted to working concentration (content verified by $A\_280$ as measured on an HP 8453 diode array spectrophotometer) and stored at 4 deg C, if stored overnight or at room temp if used the same day.

Animal Protocol—Taconic female balb/c mice (4–8 weeks old) were anesthetized with ketamine/xylazine (100/8 mg/kg), injected IP into the right side and had their left quad muscle shaved. Depth of anesthesia could be assessed by a toe pinch several minutes after IP administration. 28G insulin syringes (Becton Dickson #32943φ) were filled while the animals went asleep. Each animal received a 1×50 $\mu$l injection of V1Jns-SeAP at the plasmid concentration shown in Tables 1 and 2 (0.2 mg/ml). The plasmid DNA was injected into the shaved quad muscle. The syringe needle entered just above the knee cap and was driven approximately 1.0 cm longitudinally along the quad muscle towards the hip. Typically the syringe was immediately removed and the 2 needle electrodes were then inserted through the skin and into the outer edges of the quad muscle group parallel with the muscle fibers with the assistance of the needle/electrode holder described in FIG. 7 with a electrode separation of D=3 mm. If necessary, a sharp needle was used to puncture a hole in the skin to allow the electrode to pass.

Thus, the bubble of injectate was encompassed between the two parallel electrodes. Electro-stimulation was administered as indicated below. Bleeds typically were taken at 9 days post dose and sera separated using microtainer tubes. Sera were transferred to Eppendorf tubes and frozen until analysis. Five microliters of each serum were analyzed for SeAP level using the Tropix Phosphalight chemiluminescence assay kit (#BP300) and readings were taken using a Dynex MLX luminometer.

Electrodes—Disposable concentric conducting electrodes were obtained from Oxford Instruments Medical System Div. (West Chester, N.Y.), Medelec 27G needles, #N53155. Needle holders and cables were obtained (#N21001) and the amplifier output signals were applied between pins 4 on the DIN connectors, attached to the outer electrode of each concentric needle.

Custom made partially insulating electrodes were fabricated from the same Oxford Medelec concentric conducting electrodes (26G, 0.46 mm φ yellow hub). The electrodes were spray coated with an airbrush (Testor's Model Master #50603) with red enamel paint (Testor's Model Master #1705) thinned according to the manufacturer's instructions, and let to dry for a couple of days at room temperature. They were then clear top coated (Testor's Model Master #2736) via the airbrush again, and let to dry at least 12 more hours. It was clear from many failed attempts that controlling the radius of curvature of the tip of needle would be important. Too sharp a needle with small radius of curvature led to a very difficult surface to coat with paint. Thus, it was believed that blunting the tip by rubbing on 600 grit sandpaper or manufacturing them with greater radius of curvature would produce better coatings.

Alternatively, stainless steel monopolar needles (#PRO-37US) were purchased from The Electrode Store (Buckley, Wash.) and coated by Advanced Industrial Coatings (Stockton, Calif.) with either du Pont (Wilmington, Del.) PFA (product # 420-703, 1700-000) or Whitford (West Chester, Pa.) Xylan (product 1391, 1331 tan). Other coatings prototyped included a proprietary PTFE coating of the Electrode Store and a polyurethane coating from Hydromer Inc. (Branchburg, N.J.).

Electro-stimulation and high speed data acquisition system—Signals were generated and recorded in a personal computer based system with external custom built power amplifier. The signal generator was a National Instruments (Austin, Tex.) NI-5411 ARBitrary waveform generator card in a Dell Dimension XPS T600 (SIN W-16916) personal computer. Waveforms were designed with National Instruments Waveform Editor and stored as digital binary files at 10 Msam/sec. Text based sequence files were constructed in National Instruments Sequence Editor or Microsoft Notepad, which called these binary files to get loaded onto peripheral memory on the ARB card and played out its single 50 ohm output. The output signal was immediately split, one connection was made to an input channel on the data acquisition board, the other connection was made to the DC input of the amplifier.

The custom amplifier was built in the Merck Research Laboratories Rahway Bioelectronics Laboratory, (Model 19980664, S/N: A-IRBM) and consisted principally of an APEX Microtechnology (Tucson, Ariz.) PA-85 monolithic operational amplifier. The amplifier was operated in either a constant current (CC) or constant voltage (CV) feedback mode as indicated in Table 1. The applied I–V current and voltage monitor signals across the muscle tissue were connected directly from the voltage-sense and current-sense isolated outputs of the amplifier as indicated schematically in FIG. 1. A safety interlock pedal was installed for precaution in order to abort the electrostimulation treatment for whatever reason. A high voltage (APEX) amplifier was also coupled to provide a ±400V output if desired.

The high speed data acquisition system consisted of a National Instruments AT-MIO-16E-1 E-series multifunction multiple input data acquisition board installed next to the ARB card in the same Dell PC. Electrical signals to record were entered into a SCB-68 breakout box and shielded in a grounded aluminum foil shell to reduce RF noise. Digitized 12-bit measurements from the three input channels (ARB output, voltage applied, current applied) were streamed to hard disk at either 100 kSam/sec or 250 kSam/sec using a modified version of the National Instruments High Speed Data Logger.vi example virtual instrument code. In our case, the two National Instruments cards were jointly controlled within the LabVEW software environment by a custom written application named NI ARB/DAQ v1.x. Sometimes, a stimulation monitor box (RY-Bioelectronics #19990594) was connected in series with the electrodes-; however it is preferred not to use such a box.

Electro-stimulation treatments—Group 1 received no electrostimulation after DNA injection, Group 2 received electrostimulation through stainless steel conducting electrodes at constant current (CC, I=±50 mA). All Group 2 animals received N=10 trains of, $f$=1 kHz bipolar square wave pulses (200 $\mu$sec each polarity, 600 $\mu$sec inactive), with one second rest period between trains. Group 3 animals received electrostimulation through partially insulating painted electrodes as indicated above. Constant voltage (V=100 V) was applied to the muscle tissue and all Group 3 animals received N=10, $f$=1 kHz bipolar square wave (200

μsec each polarity, 600 μsec inactive), with one second rest period between trains.

Electro-stimulation analysis—Raw binary data files, often greater than 10 Mb per animal per treatment, could be examined and analyzed using a direct modification of National Instruments High Speed Data Reader.vi to accommodate multiple channel recordings. Additionally, other LabVIEW software was written to decimate the data and create histograms of instantaneous voltage levels and currents levels measured during the treatment process.

Figure 9A:
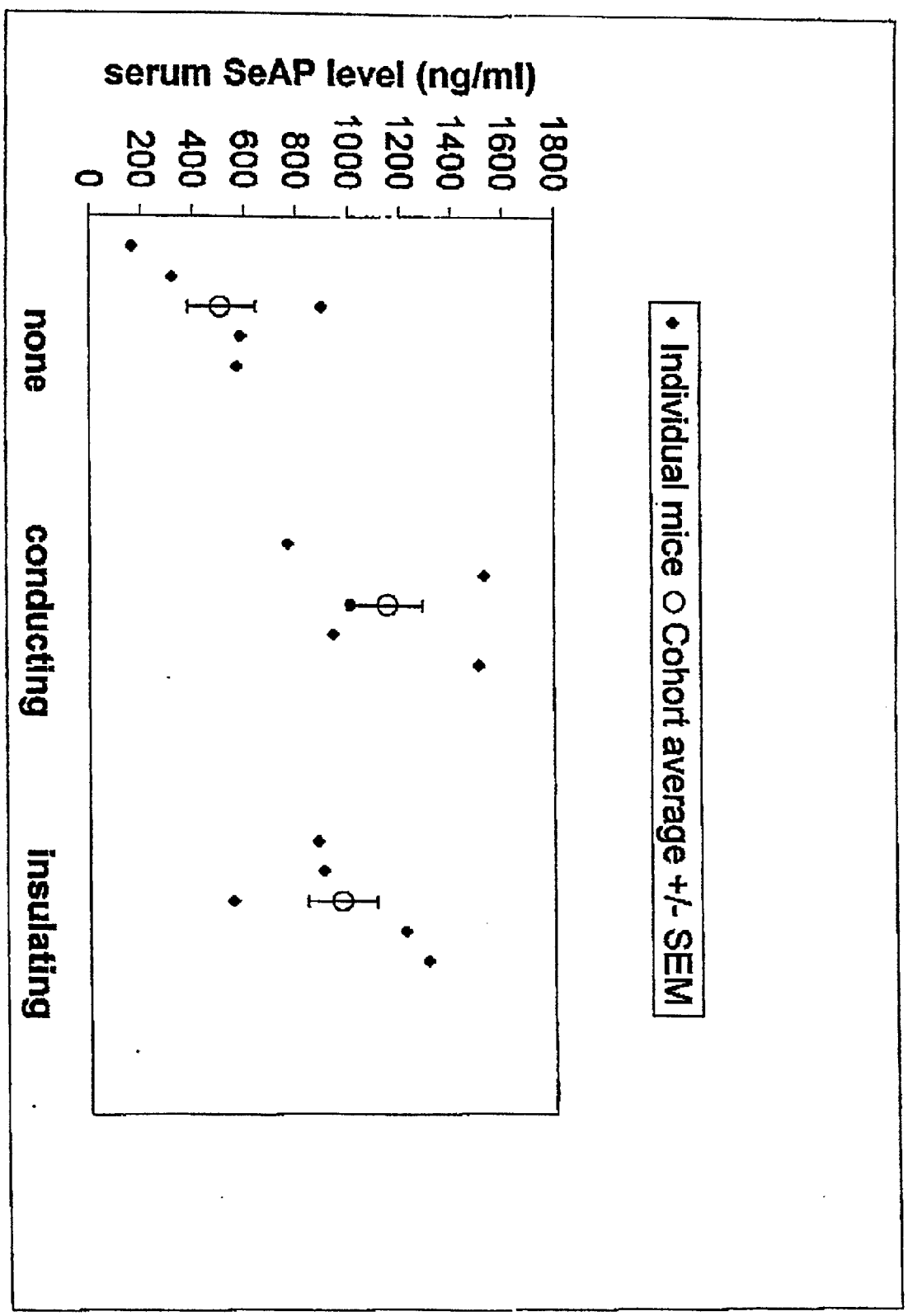
FIGS. 9A and 9B show serum SeAP levels in balb/c mice at (A) 4 days and (B) 11 days post injection, which were subjected to (i) no electrostimulation (−ES), (ii) electrostimulation with stainless steel conducting electrodes, and (iii) electrostimulation with partially insulating electrodes. Data is presented for individual mice (♦) and cohort average (○) with standard errors of the mean (SEM) indicated.
Figure 9B:
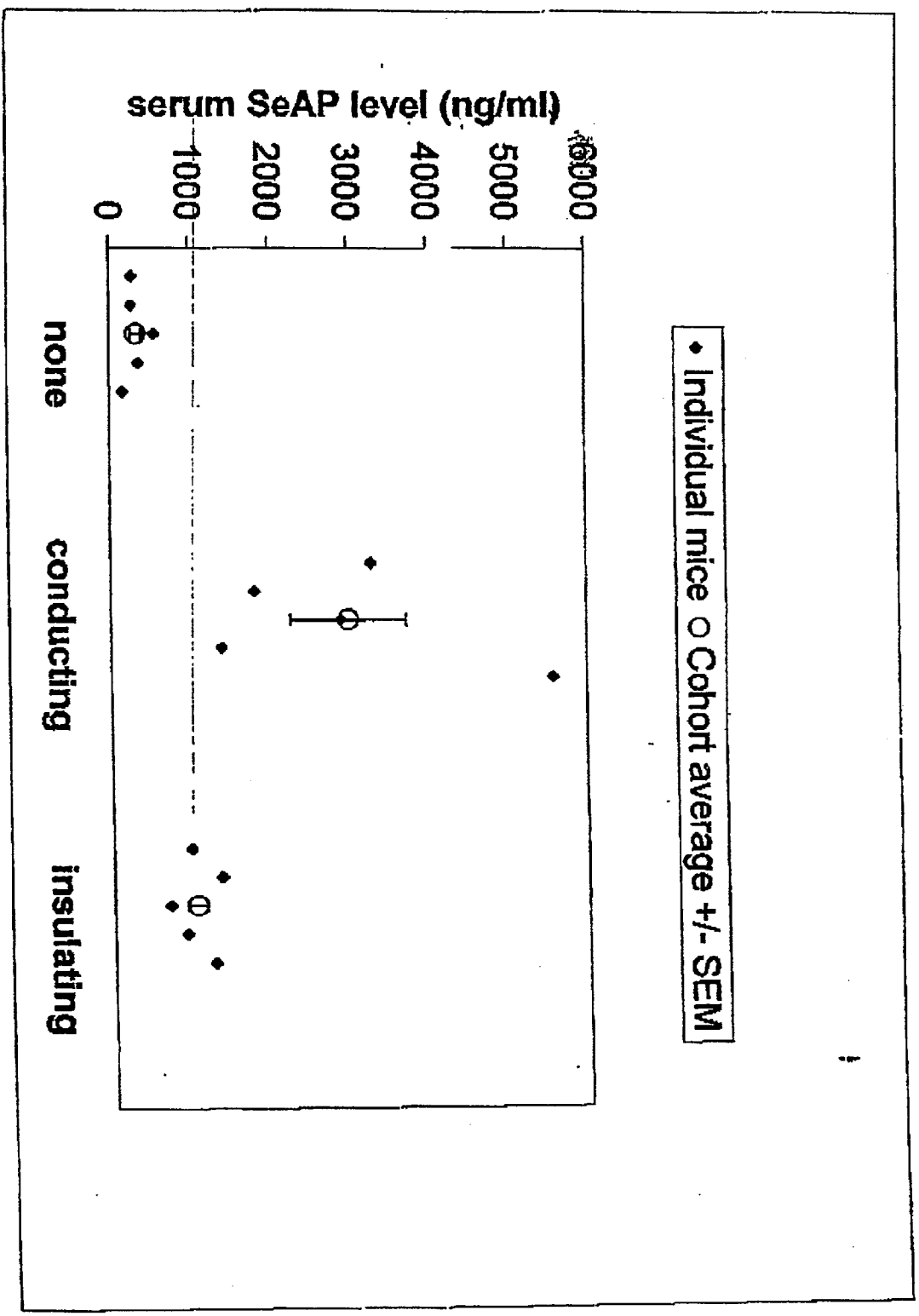

FIGS. 9A and 9B show serum SeAP levels in balb/c mice at (A) 4 days post dose and (B) 11 days post dose. FIG. 9A shows a significant and comparable enhancement in SeAP expression in mice 4 days subsequent to electrostimulation with either conducting or partially insulating electrodes. The complete data set and other parameters are shown in Table 1 (day 4 and day 11).

It has been consistently observed that animals that underwent the electrostimulation process with stainless steel conducting electrodes (group 2), experienced a significant and undesirable involuntary muscle contraction. This contraction consisted of not only the muscle under treatment, but also adjacent muscle groups. Thus if N=10 trains were applied, then 10 periods of involuntary muscle contraction were observed which exactly corresponded to the time in which signals were applied. Moreover, it was clearly observed that the severity of the muscle contraction increased with increasing current delivered. Thus with conducting electrodes, application of a 100 mA signal in CC mode lead to a more severe muscle contraction than when 50 mA was applied in otherwise identical conditions.

Quite unexpectedly and in sharp contrast to the conducting electrode case, the use of partially insulated electrodes dramatically reduced the involuntary muscle contraction observed (group 3). Typically, only an intermittent quiver or twitch of only the quad muscle under treatment was observed. Typically over the course of a 10 second treatment, three or four momentary quivers or twitches were observed.

Thus, the partially insulating electrodes of the present invention have produced enhanced biological response (FIGS. 9A–B) with decreased muscle contraction and hence increased tolerability.

Figure 10A:
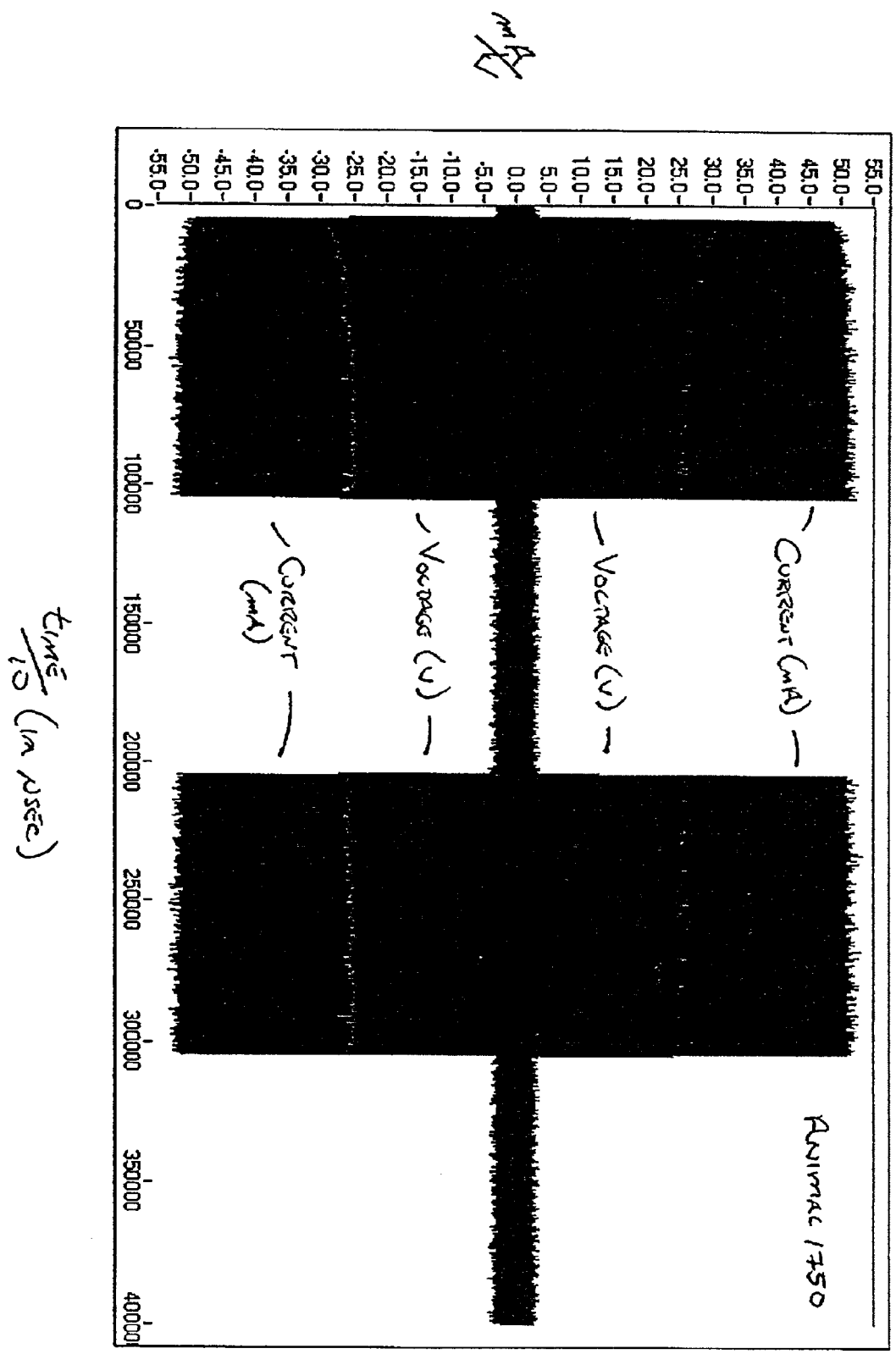
FIGS. 10A and 10B show time series graphs of the raw binary data acquired during the electric stimulation treatment process (both voltage applied in volts and current delivered in milliamps—mA) for a representative portion of the electrostimulation of animal 1750. This mouse received electrostimulation by stainless steel conducting electrodes, in constant current (CC) mode on the amplifier at approximately +50 mA and −50 mA, characteristic for the N=10 trains, $f$=1 KHz bipolar square wave (200 $\mu$sec each polarity, 600 $\mu$sec inactive). The 4 second window of time presented in FIG. 10A includes two of the ten applied trains and allows visualization of the overall or macroscopic changes in current and voltage; while the 6 mS window presented in FIG. 10B includes six of the unit cell pulses and allows examination of the individual waveform pulses delivered to the tissue load.
Figure 10B:
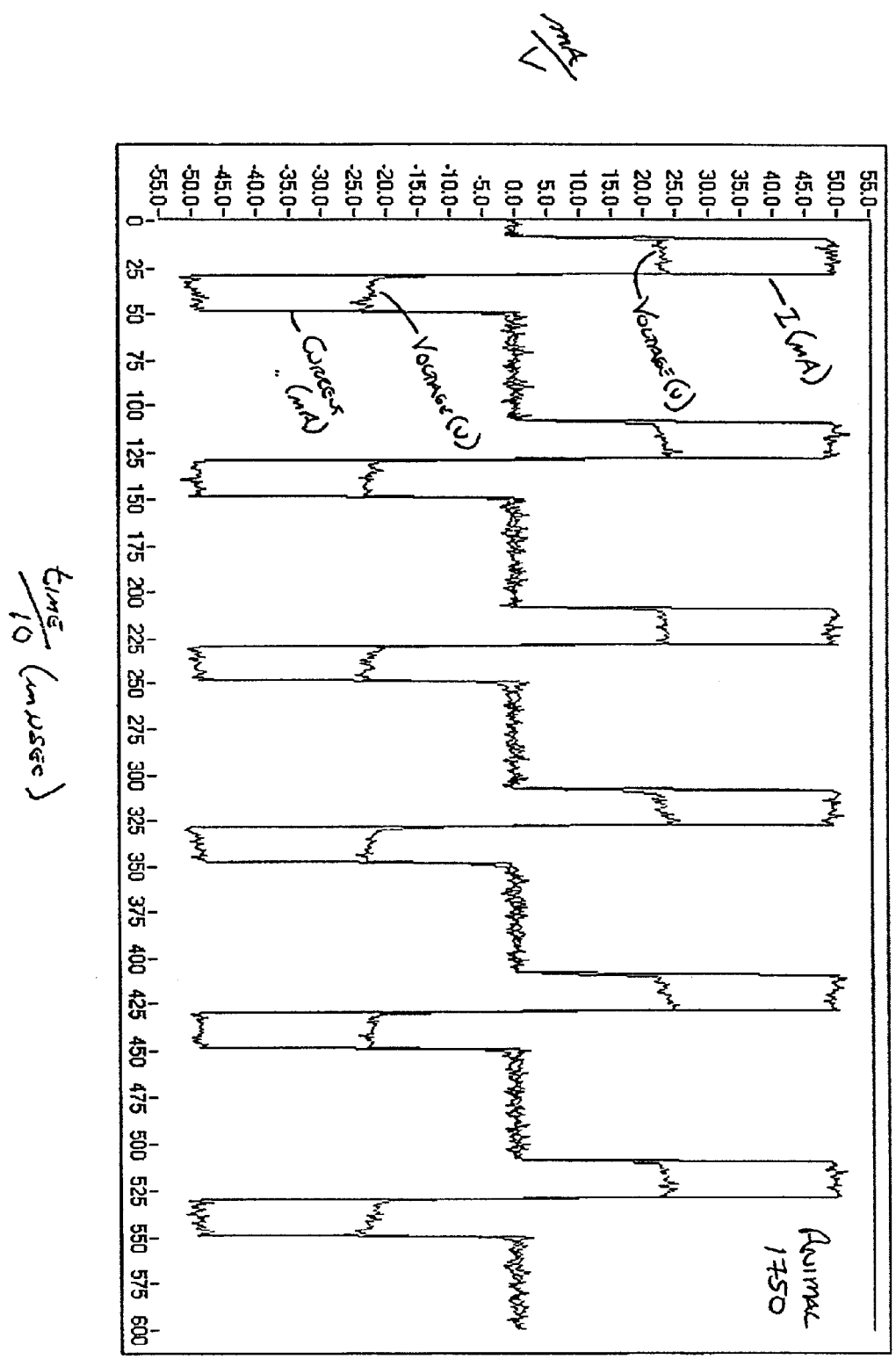

FIGS. 10A and 10B show time series graphs of the raw binary data acquired during the electrical stimulation treatment process (both voltage applied in volts and current delivered in milliamps—mA) for a representative portion of the electrostimulation of animal 1750, which received electrostimulation by a stainless steel conducting electrode in constant current (CC) mode on the amplifier at approximately+50 mA and–50 mA, characteristic for the N=10 trains, $f$=1 KHz bipolar square wave (200 μS each polarity, 600 μS inactive). The 4 second window of time presented in FIG. 10A includes 2 of the 10 applied trains and allows visualization of the overall or macroscopic changes in current and voltage; while the 6 mS window presented in FIG. 10B includes 6 of the unit cell pulses and allows examination of the individual waveform pulses delivered to the tissue load.

FIGS. 11A–D show instantaneous voltage and current histogram analysis of the raw binary data file recorded during the treatment procedure for animal 1750. FIGS. 11A and 11B provide macroscopic views, while FIGS. 11C and 11D magnify the central portion of each histogram to reveal details invisible when viewing the overall histogram. The total absolute current was $I_{tot}$=20 mA and the total charge delivered was approximately 200 mC over the 10 second treatment.

Figure 12A:
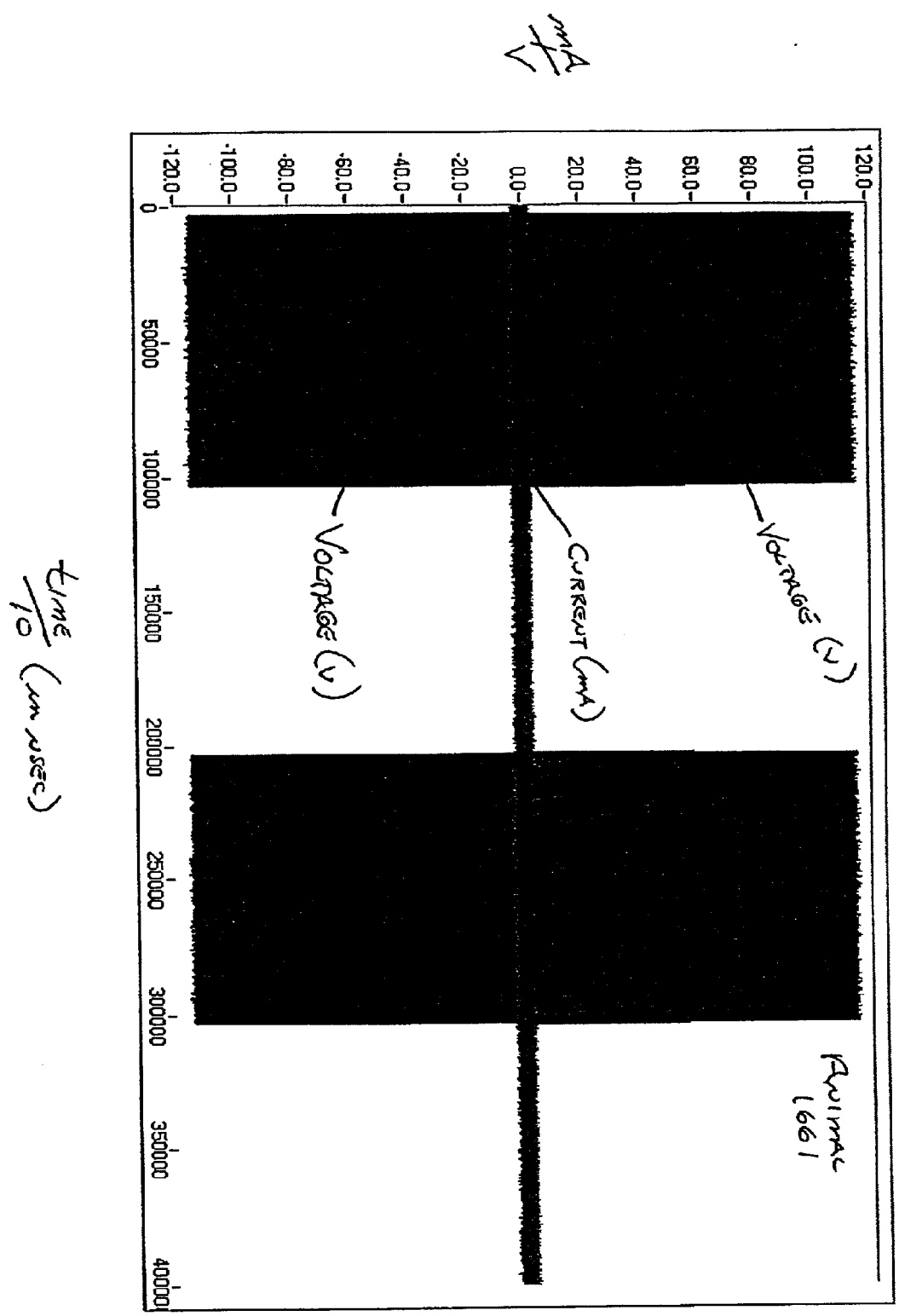
FIGS. 12A and 12B show time series graphs of the raw binary data acquired during the electrical stimulation treatment process (both voltage applied in volts and current delivered in milliamps) for a representative portion of the electrostimulation of animal 1661. This mouse received electrostimulation treatment via a partially insulating electrode, coated with enamel paint and a clear top coat, in constant voltage (CV) mode on the amplifier at approximately +100 V and −100 V, utilizing the same N=10 trains, $f$=1 KHz bipolar square wave (200 $\mu$sec each polarity, 600 $\mu$sec inactive). The 4 second window of time presented in FIG. 12A includes two of the ten applied trains and allows visualization of the overall or macroscopic changes in current and voltage; while the 6 mS window presented in FIG. 12B includes six of the unit cell pulses and allows examination of the individual waveform pulses delivered to the tissue load.
Figure 12B:
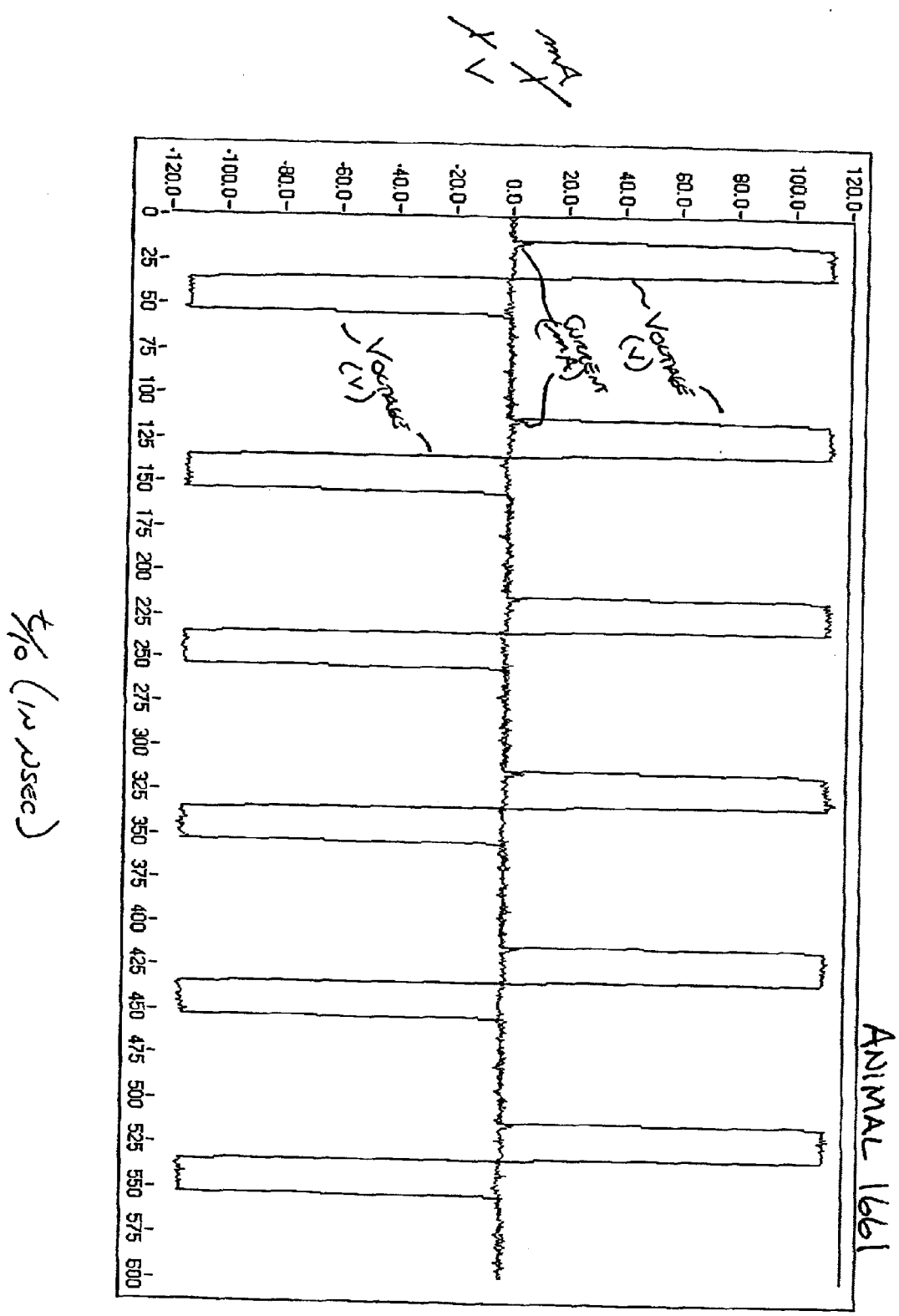

FIGS. 12A and 12B show time series graphs of the raw binary data acquired during the electrical stimulation treatment process (both voltage applied in volts and current delivered in milliamps—mA) for a representative portion of the electrostimulation of animal 1661. This mouse received electrostimulation treatment via a partially insulating electrode, coated with enamel paint and a clear top coat, in constant voltage (CV) mode on the amplifier at approximately +100 V and −100 V, utilizing the same N=10 trains, $f$=1 KHz bipolar square wave (200 μS each polarity, 600 μS inactive). The 4 second window of time presented in FIG. 12A includes 2 of the 10 applied trains and allows visualization of the overall or macroscopic changes in current and voltage; while the 6 mS window presented in FIG. 12B includes 6 of the unit cell pulses and allows examination of the individual waveform pulses delivered to the tissue load.

FIGS. 13A–D show instantaneous voltage and current histogram analysis of the raw binary data file recorded during the treatment procedure for animal 1661. FIGS. 13A and 13B provide macroscopic views, while FIGS. 13C and D magnify the central portion of each histogram to reveal details invisible when viewing the overall histogram. The total absolute current (charge) delivered was $I_{tot}$=0.8 mA (Qt≅8 mC over the 10 second treatment).

FIG. 14 shows serum SeAP levels in balb/c mice at 8 days post injection, which were subjected to (I) no electrostimulation (−ES), (ii) electrostimulation with conducting stainless steel electrodes, and (iii) electrostimulation with completely insulating PFA coated electrodes.

Example 2

Effect of Conducting and Completely Insulated Electrodes on Serum SeAP Levels in Mice V1Jns-SeAP plasmid DNA (10 (μg) was delivered to balb/c mice under electrostimulation conditions similar to Example 1 and are described in Table 2, with both stainless steel conducting (Group 2) and completely insulated dielectric electrodes (PFA coated) Group 3=square pulses N=10 trains.

In the limit of using completely insulating electrodes, there was no muscle contraction, quiver or twitch of the muscle observed during treatment. There were no visual characteristics of the treatment to enable confirmation that active signals were applied. Instead it was necessary to rely on the data acquisition system to confirm that voltage had been applied and to confirm what was clearly apparent, that no current had been delivered.

FIG. 14 further shows that serum SeAP levels for the completely insulated electrode (Group 3) were indistinguishable from no electrostimulation at all (compared to Group 1). In contrast, stainless steel electrodes (CC, I=±50 mA, N=10 trains, $f$=1 kHz bipolar square wave pulses, 200 μsec each polarity, 600 μsec inactive) provided a robust response (Group 2).

This procedure was repeated at 400V with the completely insulated PFA electrodes. No enhancement of the biological response was observed.

As discussed throughout this specification, these results show that a completely insulated dielectric electrode (i.e., which delivers no more than a baseline current or charge over background noise over the course of the treatment) does not enhance cellular delivery of a DNA plasmid expression vector. Instead, as shown in Example 1, infra, the electrodes must at least partially conduct current, albeit at a preferably lower level than the current provided through conventional stainless steel electrodes which must satisfy Ohms law, to both promote cellular transfection of nucleic acid molecules as well as reducing involuntary muscle reflexes.

The invention having been disclosed in connection with the foregoing variations and examples, additional variations will now be apparent to persons skilled in the art. The invention is not intended to be limited to the variations specifically mentioned, and accordingly reference should be made to the appended claims rather than the foregoing discussion of preferred examples, to assess the scope of the invention in which exclusive rights are claimed.

TABLE 1

| Group | Electrodes | Mode | Set point | d (mm) | tag | Conc. (ng/ml) | Day 4 Bleed SeAP Conc. (ng/ml) | SEM | Day 11 Bleed Conc. | SeAP Conc. (ng/ml) | SEM (ng/ml) |
|---|---|---|---|---|---|---|---|---|---|---|---|
| 1 | None | (−)ES | | | 1726 | 164 | | | 291 | | |
| | | | | | 1727 | 320 | | | 284 | | |
| Total absolute charge (Qt) ≅ 0.8 mC | | | | | 1728 | 584 | | | 368 | | |
| | | | | | 1729 | 573 | | | 163 | | |
| | | | | | 1730 | 900 | 508 | 126 | 566 | 334 | 67 |
| 2 | Conducting | CC | 50 mA | 3 mm | 1746 | 766 | | | 3280 | | |
| | | | | | 1747 | 1528 | | | 1801 | | |
| Total absolute charge (Qt): 1750 | | | | | 1748 | 942 | | | 1387 | | |
| (approximately 200 mC) | | | | | 1749 | 1506 | | | 5573 | | |
| | | | | | 1750 | 1007 | 1150 | 155 | 2894 | 2987 | 733 |
| 3 | Partially Insulated | CV | 100 v | 3 mm | 1661 | 883 | | | 981 | | |
| | | | | | 1662 | 902 | | | 1353 | | |
| Total absolute charge (Qt): 1661 (8 mC); 1662 (10 mC); | | | | | 1663 | 1219 | | | 913 | | |
| 1663 (10 mC); 1664 (13 mC); 1665 (20 mC) | | | | | 1664 | 1307 | | | 1266 | | |
| | | | | | 1665 | 552 | 973 | 135 | 709 | 1044 | 118 |

TABLE 2

| | Vaccine | Conditions | tag/ID | x-axis value | SeAP Conc. (Ng/ml) | Cohort Average | Cohort SEM |
|---|---|---|---|---|---|---|---|
| Grp 1 | 10 μg V1JnsSEAP | No ES | 4561 | 1 | 372 | | |
| | | | 4562 | 2 | 349 | | |
| | | | 4563 | 4 | 674 | | |
| | | | 4564 | 5 | 696 | | |
| | | | 4565 | 3 | 277 | 474 | 88 |
| Grp 2 | 10 μg V1JnsSEAP | Conducting | 4566 | 11 | 4040 | | |
| | | Stainless Steel | 4567 | 12 | 6430 | | |
| | | CC 50 mA | 4568 | 14 | 8756 | | |
| | | 200/200/600 sq. | 4569 | 15 | 6360 | | |
| | | N = 10 trains | 4570 | 13 | 15611 | 8245 | 1984 |
| Grp 3 | 10 μg V1JnsSEAP | Insulating | 4581 | 21 | 434 | | |
| | | PFA | 4582 | 22 | 674 | | |
| | | CV 100 V | 4583 | 24 | 810 | | |
| | | 200/200/600 sq. | 4584 | 25 | 958 | | |
| | | N = 10 trains | 4585 | 23 | 624 | 700 | 88 |

What is claimed is:

1. A method for delivering a pharmaceutical agent to a host comprising the steps of:
providing at least one elongated electrode with a conductive material enclosed within a partially conductive outer surface;
inserting the electrode so as to pierce a host tissue;
infusing the host tissue with the pharmaceutical agent;
electrically stimulating the host tissue using a signal generator coupled between the electrode and a remote point, the signal generator being operable to deliver an at least partially periodic signal to the electrode; and,
wherein the Dartially conductive outer surface of the electrode limits electrical current coupled into the host tissue from the signal generator.

2. The method of claim 1 further comprising the steps of inserting at least one second electrode into the host tissue, also having a partially conductive outer surfaces and wherein a portion of the body substantially between the electrodes is electrically stimulated by coupling the signal generator to each said electrode, the signal generator being operable to deliver an at least partially periodic signal to the electrodes.

3. The method of claim 2 wherein the signal generator is operated in a controlled voltage mode.

4. The method of claim 1 wherein the signal generator is operable to deliver about ±100 to ±400 volts.

5. The method of claim 1 comprising operating the signal generator such that the partially conductive outer surface of the electrode couples electrical current into the host tissue from the signal generator sufficient to deliver a charge in the range of 5–20 millicoulombs per periodic cycle.

6. The method of claim 1, wherein the host tissue comprises skeletal muscle.

7. A method of electrically stimulating the cellular delivery of a pharmaceutical agent in vivo within a tissue of a mammalian host, which comprises:
applying an electrode configuration to a portion of the mammalian host, including penetrating the host tissue with at least one elongated conductive electrode within a partially conductive outer surface;

infusing the portion of the mammal with a pharmaceutical agent, adjacent to the electrode; and, establishing an electric field of a predetermined potential between the electrode and a point spaced from the electrode by the portion thus infused;

wherein electric current coupled into the portion from the electric field is limited by said partially conductive outer surface to an amplitude that is less than a current that would be predicted to flow under Ohm's law from the conductive electrode within the partially conductive outer surface.

8. The method of claim 7 wherein the pharmaceutical agent comprises a nucleic acid molecule.

9. The method of claim 7 wherein the nucleic acid molecule comprises a DNA plasmid expression vector.

10. The method of claim 7 wherein the mammalian host is a human.

11. The method of claim 7 wherein the pharmaceutical agent comprises a nucleic acid molecule.

12. The method of claim 11 wherein the nucleic acid molecule comprises a DNA plasmid expression vector.

13. The method of claim 7 wherein the pharmaceutical agent comprises a protein.

14. The method of claim 7 wherein the pharmaceutical agent comprises an organic molecule.

15. The method of claim 7, wherein the host tissue comprises skeletal muscle.

16. A method of electrically stimulating the cellular delivery of a pharmaceutical agent in vivo within a mammalian host tissue, which comprises:

applying an electrode configuration to a portion of a mammal, including penetrating the host tissue with at least one elongated conductive electrode within a partially conductive outer surface;

infusing the portion of the mammal with a pharmaceutical agent, adjacent ot the electrode;

establishing an electric field of a predetermined potential between the electrode and a point spaced from the electrode by the portion thus infused;

wherein electric current coupled into the portion from the electric field is limited by said partially conductive outer surface to an amplitude that is less than a current that would be predicted to flow under Ohm's law from the conductive electrode within the partially conductive outer surface;

measuring and recording a voltage and current delivered to the portion of the mammal while electrically stimulating the portion of the mammal; and, establishing a potential at which the current coupled into the portion by said electric field provides electric stimulus without measurable involuntary muscle reflexes during a course of treatment.

17. The method of claim 16 wherein the pharmaceutical agent comprises a nucleic acid molecule.

18. The method of claim 17 wherein the nucleic acid molecule comprises a DNA plasmid expression vector.

19. The method of claim 16 wherein the mammal is a human.

20. The method of claim 19 wherein the pharmaceutical agent comprises a nucleic acid molecule.

21. The method of claim 20 wherein the nucleic acid molecule comprises a DNA plasmid expression vector.

22. The method of claim 16 wherein the pharmaceutical agent comprises a protein.

23. The method of claim 16 wherein the pharmaceutical agent comprises an organic molecule.

24. The method of claim 16, wherein the host tissue comprises skeletal muscle.

* * * * *